United States Patent
Garza et al.

(10) Patent No.: US 10,188,052 B2
(45) Date of Patent: Jan. 29, 2019

(54) MAIZE PLANTS WITH IMPROVED PATHOGEN RESISTANCE

(71) Applicant: MONSANTO TECHNOLOGY LLC, St. Louis, MO (US)

(72) Inventors: Isidro Alvarez Garza, Zapopan (MX); Romain Jean-Baptiste Fouquet, Saint-Palais (FR); Hongwu Jia, Morrisville, NC (US); Yule Pan, Chesterfield, MO (US)

(73) Assignee: Monsanto Technology LLC, St. Louis, MO (US)

(*) Notice: Subject to any disclaimer, the term of this patent is extended or adjusted under 35 U.S.C. 154(b) by 73 days.

(21) Appl. No.: 14/811,697

(22) Filed: Jul. 28, 2015

(65) Prior Publication Data

US 2016/0057952 A1    Mar. 3, 2016

Related U.S. Application Data

(60) Provisional application No. 62/043,181, filed on Aug. 28, 2014, provisional application No. 62/101,302, filed on Jan. 8, 2015.

(51) Int. Cl.
*A01H 5/10* (2018.01)
*A01H 1/04* (2006.01)
*C12Q 1/6895* (2018.01)

(52) U.S. Cl.
CPC .............. *A01H 1/04* (2013.01); *C12Q 1/6895* (2013.01); *C12Q 2600/13* (2013.01); *C12Q 2600/156* (2013.01)

(58) Field of Classification Search
None
See application file for complete search history.

(56) References Cited

U.S. PATENT DOCUMENTS 8,367,906 B2    2/2013  Bockelman

OTHER PUBLICATIONS

Civardi et al., 1994, Proc. Natl. Acad. Sci. USA 91: 8268-8271.*
Arizona Genomics Institute B73 RefGen_v2 sequence, available at http://www.genome.arizona.edu/modules/publisher/item.php?itemid=16, accessed Nov. 11, 2016.
Bajet et al., "Control of tar spot of maize and its effect on yield," *International Journal of Pest Management*, 40:121-125, 1994.
Ceballos et al., "Inheritance of resistance to tar spot complex in maize," *Phytopathology*, 82(5):505-512, 1992.
Hock et al., "Sequential development of pathogens in the maize tarspot disease complex," *Mycopatholgia*, 117:157-161, 1992.
Hock et al., "Studies on the epidemiology of the tar spot disease complex of maize in Mexico," *Plant Pathology*, 44:490-502, 1995.
IBM2 2008 Neighbors Maize Genomic Map, available at http://www.maizegdb.org, accessed Nov. 11, 2016.

* cited by examiner

*Primary Examiner* — Amjad Abraham
*Assistant Examiner* — Bratislav Stankovic
(74) *Attorney, Agent, or Firm* — Dentons US LLP; Matthew Madsen Esq.

(57) ABSTRACT

The present invention provides methods and compositions for producing elite lines of corn exhibiting improved resistance to TARSC. Also provided in the present invention are corn plants exhibiting TARSC resistance resulting from such methods, and methods for breeding corn such that the TARSC resistance traits may be transferred to a desired genetic background.

49 Claims, No Drawings
Specification includes a Sequence Listing.

MAIZE PLANTS WITH IMPROVED PATHOGEN RESISTANCE

REFERENCE TO RELATED APPLICATIONS

This application claims the benefit of U.S. Provisional Application No. 62/043,181, filed Aug. 28, 2014, and U.S. Provisional Application No. 62/101,302, filed Jan. 8, 2015, each of which is herein incorporated by reference in its entirety.

FIELD OF THE INVENTION

The present invention relates to the field of agricultural biotechnology. More specifically, the invention relates to methods for producing corn plants with improved pathogen resistance.

INCORPORATION OF SEQUENCE LISTING

A sequence listing contained in the file named "MONS367US_ST25.txt" which is 9,529 bytes (measured in MS-Windows®) and created on Jul. 27, 2015, and comprises 40 nucleotide sequences, is filed electronically herewith and incorporated by reference in its entirety.

BACKGROUND OF THE INVENTION

Advances in molecular genetics have made it possible to select plants based on genetic markers linked to traits of interest, a process called marker-assisted selection (MAS). While breeding efforts to date have provided a number of useful corn lines and varieties with beneficial traits, there remains a need in the art for selection of varieties with further improved traits and methods for their production. In many cases, such efforts have been hampered by difficulties in identifying and using alleles conferring beneficial traits. These efforts can be confounded by the lack of definitive phenotypic assays, as well as other issues such as epistasis and polygenic or quantitative inheritance. In the absence of molecular tools such as MAS, it may not be practical to attempt to produce certain new genotypes of crop plants due to such challenges.

SUMMARY OF THE INVENTION

In one aspect, the present invention provides methods of obtaining corn plants with improved tar spot complex (TARSC) resistance comprising: a) providing a population of corn plants; b) detecting in said population a plant comprising a TARSC resistance allele at a polymorphic locus in, or genetically linked to, a chromosomal segment between 0 cM (0 IcM) and 17.8 cM (approximately 74.5 IcM) on chromosome 10; and c) selecting said plant from said population based on the presence of said allele. In some embodiments, said segment is flanked by loci SEQ ID NO: 1 and SEQ ID NO: 7 on chromosome 10 or flanked by loci SEQ ID NO: 4 and SEQ ID NO: 6 on chromosome 10. In other embodiments, said segment is located between 3.99 cM (approximately 8 IcM) and 17.7 cM (approximately 74.1 IcM), between 9.4 cM (approximately 35.8 IcM) and 13.7 cM (approximately 57.5 IcM), or between 8.3 cM (approximately 31.9 IcM) and 11.9 cM (approximately 50.2 IcM) on chromosome 10. In yet other embodiments, said polymorphic locus comprises a sequence selected from the group consisting of SEQ ID NOs: 1, 2, 3, 4, 5, 6, 7, and 36. In certain embodiments, a plant obtained by the methods provided by the invention exhibits increased yield relative to a control plant not comprising said TARSC resistance allele. In some embodiments, step (a) of providing comprises crossing a first corn plant comprising a TARSC resistance allele with a second corn plant to produce a population of corn plants. In other embodiments, producing the population of corn plants comprises backcrossing. In further embodiments, step (b) of detecting comprises the use of an oligonucleotide probe.

In another aspect, the invention provides methods of producing corn plants with improved tar spot complex (TARSC) resistance comprising: a) crossing a first corn plant comprising a TARSC resistance allele with a second corn plant of a different genotype to produce one or more progeny plants; and b) selecting a progeny plant based on the presence of said allele at a polymorphic locus in, or genetically linked to, a chromosomal segment between 0 cM (0 IcM) and 17.8 cM (approximately 74.5 IcM) on chromosome 10; wherein said allele confers improved TARSC resistance compared to a plant lacking said allele. In some embodiments, said segment is flanked by loci SEQ ID NO: 1 and SEQ ID NO: 7 on chromosome 10 or flanked by loci SEQ ID NO: 4 and SEQ ID NO: 6 on chromosome 10. In other embodiments, said segment is located between 3.99 cM (approximately 8 IcM) and 17.7 cM (approximately 74.1 IcM), between 9.4 cM (approximately 35.8 IcM) and 13.7 cM (approximately 57.5 IcM), or between 8.3 cM (approximately 31.9 IcM) and 11.9 cM (approximately 50.2 IcM) on chromosome 10. In further embodiments, said polymorphic locus comprises a polynucleotide comprising a sequence selected from the group consisting of SEQ ID NOs: 1, 2, 3, 4, 5, 6, 7, and 36. In yet further embodiments, said plant exhibits increased yield relative to a control plant not comprising said TARSC resistance allele. In some embodiments, the methods provided by the invention further comprise: c) crossing said progeny plant with itself or a second plant to produce one or more further progeny plants; and d) selecting a further progeny plant comprising said allele. In certain embodiments, step (d) of selecting comprises marker-assisted selection. In other embodiments, said marker-assisted selection comprises selecting a progeny plant based on the presence of said allele in at least one polymorphic sequence selected from the group consisting of SEQ ID NOs: 1, 2, 3, 4, 5, 6, 7, and 36. In further embodiments, said further progeny plant is an F2-F7 progeny plant. In yet further embodiments, producing the progeny plant comprises backcrossing. In some embodiments, backcrossing comprises from 2-7 generations of backcrosses. In other embodiments, backcrossing comprises marker-assisted selection. In further embodiments, backcrossing comprises marker-assisted selection in at least two generations. In yet further embodiments, backcrossing comprises marker-assisted selection in all generations. In some embodiments, marker-assisted selection comprises selecting a progeny plant based on the presence of said allele in at least one polymorphic locus selected from the group consisting of: SEQ ID NOs: 1, 2, 3, 4, 5, 6, 7, and 36. In other embodiments, said first corn plant is an inbred or a hybrid. In further embodiments, said second corn plant is an agronomically elite corn plant. In yet further embodiments, said agronomically elite corn plant is an inbred or a hybrid.

In other aspects, the present invention provides a corn plant produced by the methods of the present invention, or a plant part of said corn plant, or a seed that produces said corn plant.

In some aspects, corn plants or methods disclosed herein are used in combination with one or more pesticides including, but not limited to, herbicides, fungicides, insecticides, microbiocides, nematicides, insect repellents, bactericides, and other substances used to control pests. In other aspects, the corn plants or methods disclosed herein are used in combination with one or more triazoles, strobilurins, acy-lamino acids, pyrimidines, pyridines, aryl phenyl ketones, amides, benzanilides, imidazoles, dinitrophenols, morpholines, phenylsulfamides and organophosphorus cpds, derivatives thereof and combinations thereof which may be applied as seed, foliar, drench or drip treatments.

DETAILED DESCRIPTION OF THE INVENTION

Tar spot complex (TARSC) in maize plants results from a combination of various pathogens, including *Phyllachora maydis, Monographella maydis*, and *Coniothyrium phyllachorae*. TARSC severely impacts yield in maize crops, resulting in approximately 1.2 million tons of grain yield loss annually. Efforts to identify or produce plant lines resistant to TARSC have been hindered by a limited understanding of the genetic loci controlling TARSC resistance and a lack of available markers for detecting and tracking TARSC resistance in plants. Yield loss due to TARSC therefore remains a significant problem.

The present invention provides previously-unknown genetic loci which confer TARSC resistance and novel molecular markers linked to TARSC resistance in plants. The invention further provides methods for introgression of genetic loci conferring TARSC resistance into plant varieties previously lacking such loci, thereby providing plants with a new or improved disease resistance. Plants provided by the invention comprising these loci exhibit increased yield compared with control plants lacking the TARSC resistance loci. The genetic loci, markers, and methods provided by the invention therefore represent a significant advance in the art, enabling production of new varieties exhibiting TARSC resistance and increased yield.

In some embodiments, the invention therefore provides quantitative trait loci (QTL) that demonstrate significant co-segregation with TARSC resistance. The QTL of the invention can be tracked during plant breeding or introgressed into a desired genetic background in order to provide novel plants exhibiting TARSC resistance and one or more other beneficial traits. In particular embodiments, the invention identifies for the first time a QTL on chromosome 10 of the corn genome, designated TARSC-10.01, which is associated with TARSC resistance.

In other embodiments, the invention provides molecular markers linked to the QTL of the invention and methods of using the markers for detection of and selection for TARSC resistance. Embodiments of the invention therefore include specific markers, chromosome intervals comprising the markers, and methods of detecting markers genetically linked to TARSC-10.01 to identify disease resistant plant lines. For example, the invention provides a chromosome interval associated with TARSC resistance which is located in the region between 0 cM and 17.8 cM on chromosome 10 on Monsanto's internal consensus genetic map or between 0 IcM and 74.5 IcM on the Neighbors 2008 maize genomic map, or between 3.99 cM and 17.7 cM on Monsanto's internal consensus genetic map or between approximately 8 IcM and 74.1 IcM on the Neighbors 2008 maize genomic map (publicly available at Maize GDB website). This interval may comprise any of the markers listed in Tables 5 or 10, or one or more markers having SEQ ID NOs: 1, 2, 3, 4, 5, 6, 7, or 36, or any other markers genetically linked thereto.

The invention further provides subintervals associated with TARSC resistance which are located between 9.4 cM and 13.7 cM or between 8.3 cM and 11.9 cM on Monsanto's internal consensus genetic map (between approximately 35.8 IcM and 57.5 IcM or between approximately 31.9 IcM and 50.2 IcM, respectively, on the Neighbors 2008 maize genomic map). The invention also provides chromosome intervals associated with TARSC resistance which are flanked by loci SEQ ID NO: 1 and SEQ ID NO: 7, or flanked by SEQ ID NO: 4 and SEQ ID NO: 6.

As used herein, "cM" refers to the classical definition of a centimorgan (Haldane, 1919, J Genet, 8:299-309) wherein one cM is equal to a 1% chance that a trait at one genetic locus will be separated from a trait at another locus due to crossing over in a single generation (meaning the traits cosegregate 99% of the time during meiosis), and this definition is used herein to delineate map locations pertaining to this invention. "IcM" refers to the map units of the IBM2 2008 Neighbors Genetic Map, which was generated with an intermated recombinant inbred population (syn 4) that resulted in approximately a four-fold increase in the number of meioses as compared to the typical recombination experiment that is used to generate centiMorgan (cM) distances (Lee, et al., 2002, *Plant Mol Biol* 48:453 and the Maize Genetics and Genomics Database). Alignments between Monsanto's internal consensus genetic map and the Neighbors 2008 maize genomic map are provided, for example in Tables 7 and 12. One of skill in the art would recognize that genetic maps may be modified or updated with new information over time, and that there may be slight variation between genetic maps based on variations in the data from which the maps are derived. The chromosome intervals provided herein have been linked with TARSC resistance in plants as shown in the examples, and the ability of these intervals to confer TARSC resistance is not altered by future modifications or variations between genetic maps.

Also provided herein are markers that are useful for detecting the presence or absence of disease resistance alleles within the QTL of the invention that can be used in marker assisted selection (MAS) breeding programs to produce plants with improved resistance to TARSC infection. Markers provided by the invention include markers having SEQ ID NOs: 1, 2, 3, 4, 5, 6, 7, and 36, markers listed in Tables 5 or 10, and any other markers genetically linked thereto.

The invention further provides methods of using the markers identified herein to introgress loci associated with TARSC resistance into plants. Thus, one skilled in the art can use the invention to create novel maize plants with TARSC resistance by crossing a donor line comprising a QTL associated with TARSC resistance into any desired recipient line, with or without MAS. Resulting progeny can be selected to be genetically similar to the recipient line except for the TARSC resistance QTL.

Quantitative Trait Loci

The term "chromosome interval" designates a contiguous linear span of genomic DNA that resides on a single chromosome. A chromosome interval may comprise a QTL linked with a genetic trait and the QTL may comprise a single gene or multiple genes associated with the genetic trait. The boundaries of a chromosome interval comprising a QTL are drawn such that a marker that lies within the chromosome interval can be used as a marker for the genetic trait, as well as markers genetically linked thereto. Each interval comprising a QTL comprises at least one gene conferring a given trait, however knowledge of how many genes are in a particular interval is not necessary to make or practice the invention, as such an interval will segregate at meiosis as a linkage block. In accordance with the invention, a chromosomal interval comprising a QTL may therefore be readily introgressed and tracked in a given genetic background using the methods and compositions provided herein.

Identification of chromosomal intervals and QTL is therefore beneficial for detecting and tracking a genetic trait, such as TARSC resistance, in plant populations. In some embodiments, this is accomplished by identification of markers linked to a particular QTL. The principles of QTL analysis and statistical methods for calculating linkage between markers and useful QTL include penalized regression analysis, ridge regression, single point marker analysis, complex pedigree analysis, Bayesian MCMC, identity-by-descent analysis, interval mapping, composite interval mapping (CIM), and Haseman-Elston regression. QTL analyses may be performed with the help of a computer and specialized software available from a variety of public and commercial sources known to those of skill in the art.

In some embodiments, the invention provides a chromosomal interval comprising a QTL associated with TARSC resistance. The invention also provides multiple markers associated with TARSC resistance, for example the markers having the sequence of SEQ ID NOs: 1, 2, 3, 4, 5, 6, 7, and 36, markers listed in Tables 5 or 10, and any other markers genetically linked thereto. The invention therefore provides plants comprising a nucleic acid molecule selected from the group consisting of SEQ ID NOs: 1, 2, 3, 4, 5, 6, 7, and 36, markers listed in Tables 5 or 10, fragments thereof, or complements thereof. The present invention further provides a plant comprising alleles of the chromosome interval linked to TARSC resistance or fragments and complements thereof as well as any plant comprising any combination of one or more disease resistance loci selected from the group consisting of SEQ ID NOs: 1, 2, 3, 4, 5, 6, 7, and 36, or loci listed in Tables 5 or 10. Plants provided by the invention may be homozygous or heterozygous for such alleles. Plants provided by the invention comprising TARSC resistance alleles at these loci provided by the invention exhibit increased yield compared with control plants lacking the TARSC resistance alleles at these loci.

In one embodiment, a chromosome interval associated with TARSC resistance is flanked by loci SEQ ID NO: 1 and SEQ ID NO: 7, and is located in the region between 0 cM and 17.8 cM on chromosome 10 on Monsanto's internal consensus genetic map or between 0 IcM and 74.5 IcM on the Neighbors 2008 maize genomic map, or between 3.99 cM and 17.7 cM on Monsanto's internal consensus genetic map or between approximately 8 IcM and 74.1 IcM on the Neighbors 2008 maize genomic map (publicly available at Maize GDB website). This chromosome interval may contain one or more of SEQ ID NOs: 1, 2, 3, 4, 5, 6, 7, and 36. This chromosome interval encompasses markers that co-segregate with TARSC resistance in a given population at a p-value ≤0.05. An example of a subinterval associated with TARSC resistance includes the interval flanked by loci SEQ ID NO: 4 and SEQ ID NO: 6 which is located between 9.4 cM and 13.7 cM on Monsanto's internal consensus genetic map (between approximately 35.8 IcM and 57.5 IcM on the Neighbors 2008 maize genomic map), which defines a chromosome interval encompassing markers that co-segregate with TARSC resistance in populations studied at a p-level ≤0.05. A further example of a subinterval associated with TARSC resistance includes the interval located between 8.3 cM and 11.9 cM on Monsanto's internal consensus genetic map (between approximately 31.9 IcM and 50.2 IcM on the Neighbors 2008 maize genomic map), which defines a chromosome interval encompassing markers that co-segregate with TARSC resistance in populations studied at a p-level ≤0.05.

Thus, one skilled in the art can use the invention to create novel maize plants with TARSC resistance by associating disease resistance phenotypes with genotypes at previously unknown disease resistance loci in the maize genome. Disclosed herein are chromosome intervals that comprise alleles responsible for phenotypic differences between TARSC resistant and TARSC susceptible corn lines. The chromosome intervals of the invention are characterized in specific embodiments by genomic regions including the regions between SEQ ID NO: 1 and SEQ ID NO: 7, located between 0 cM and 17.8 cM on chromosome 10 on Monsanto's internal consensus genetic map or between 0 IcM and 74.5 IcM on the Neighbors 2008 maize genomic map, or between 3.99 cM and 17.7 cM on Monsanto's internal consensus genetic map or between approximately 8 IcM and 74.1 IcM on the Neighbors 2008 maize genomic map; regions between SEQ ID NO: 4 and SEQ ID NO: 6, located between 9.4 cM and 13.7 cM on Monsanto's internal consensus genetic map or between approximately 35.8 IcM and 57.5 IcM on the Neighbors 2008 maize genomic map; and regions between 8.3 cM and 11.9 cM on Monsanto's internal consensus genetic map or between approximately 31.9 IcM and 50.2 IcM on the Neighbors 2008 maize genomic map, and intervals which comprise markers within or genetically linked to TARSC-10.01. The invention also comprises other intervals closely linked to those intervals.

Examples of markers useful for identifying and tracking TARSC resistance alleles comprise the SNP markers listed in Tables 5, or 10, or any marker linked thereto, including a marker that maps within or is genetically linked to the chromosome intervals described herein, including the termini of the intervals. Such markers can be assayed simultaneously or sequentially in a single sample or population of samples.

Accordingly, the compositions and methods of the present invention can be utilized to guide MAS or breeding maize varieties with a desired complement (set) of allelic forms of chromosome intervals associated with superior agronomic performance (resistance, along with any other available markers for yield, disease resistance, etc.). Any of the disclosed marker alleles can be introduced into a corn line via introgression, by traditional breeding (or introduced via transformation, or both) to yield a corn plant with superior agronomic performance. The number of alleles associated with resistance that can be introduced or be present in a corn plant of the present invention ranges from 1 to the number of alleles disclosed herein, each integer of which is incorporated herein as if explicitly recited.

MAS using additional markers flanking either side of the DNA locus provide further efficiency because an unlikely double recombination event would be needed to simultaneously break linkage between the locus and both markers. Moreover, using markers tightly flanking a locus, one skilled in the art of MAS can reduce linkage drag by more accurately selecting individuals that have less of the potentially deleterious donor parent DNA. Any marker linked to or among the chromosome intervals described herein can thus find use within the scope of this invention.

Similarly, by identifying plants lacking a desired marker locus, susceptible or less resistant plants can be identified, and eliminated from subsequent crosses. These marker loci can be introgressed into any desired genomic background, germplasm, plant, line, variety, etc., as part of an overall MAS breeding program designed to enhance disease resistance. The invention also provides chromosome QTL intervals that can be used in MAS to select plants that demonstrate disease resistance or improved tolerance. The QTL intervals can also be used to counter-select plants that are susceptible or have reduced resistance to disease.

The present invention also extends to a method of making a progeny corn plant and the resulting progeny corn plants. The method comprises, in an embodiment, crossing a first parent corn plant with a second corn plant and growing the female corn plant parent under plant growth conditions to yield corn plant progeny. Methods of crossing and growing corn plants are well within the ability of those of ordinary skill in the art. Such corn plant progeny can be assayed for alleles associated with TARSC resistance as disclosed herein and, thereby, the desired progeny selected. Such progeny plants or seed thereof can be sold commercially for corn production, used for food, processed to obtain a desired constituent of the corn, or further utilized in subsequent rounds of breeding. At least one of the first or second corn plants is a corn plant of the present invention in that it comprises at least one of the allelic forms of the markers of the present invention, such that the progeny are capable of inheriting the allele.

Often, a method of the present invention may be applied to at least one related corn plant such as from progenitor or descendant line in the subject corn plants' pedigree such that inheritance of the desired resistance allele can be traced. The number of generations separating the corn plants being subjected to the methods of the present invention may be, in specific embodiments, from 1 to 20, commonly 1 to 5, and including 1, 2, or 3 generations of separation, and often a direct descendant or parent of the corn plant will be subject to the method (i.e., one generation of separation).

Thus, the invention permits one skilled in the art to detect the presence or absence of disease resistance genotypes in the genomes of corn plants as part of a MAS program. In one embodiment, a breeder ascertains the genotype at one or more markers for a disease resistant parent, which contains a disease resistance allele, and the genotype at one or more markers for a susceptible parent, which lacks the resistance allele. For example, the markers of the present invention can be used in MAS in crosses involving elite and exotic corn lines by subjecting the segregating progeny to MAS to maintain disease resistance alleles, or alleles associated with yield under disease conditions. A breeder can then reliably track the inheritance of the resistance alleles through subsequent populations derived from crosses between the two parents by genotyping offspring with the markers used on the parents and comparing the genotypes at those markers with those of the parents. Depending on how tightly linked the marker alleles are with the trait, progeny that share genotypes with the disease resistant parent can be reliably predicted to express the resistant phenotype and progeny that share genotypes with the disease susceptible parent can be reliably predicted to express the susceptible phenotype. Thus, the laborious, inefficient, and potentially inaccurate process of manually phenotyping the progeny for disease resistance is avoided.

By providing the positions in the maize genome of the intervals and the disease resistance associated markers within those intervals, the invention also allows one skilled in the art to identify and use other markers within the intervals disclosed herein or linked to the intervals disclosed herein. Having identified such regions, these markers can be readily identified from public linkage maps.

Closely linked markers flanking the locus of interest that have alleles in linkage disequilibrium with a resistance allele at that locus may be effectively used to select for progeny plants with enhanced resistance to disease conditions. Thus, the markers described herein, such as those listed in Tables 5 or 10, as well as other markers genetically linked to the same chromosome interval, may be used to select for maize plants with enhanced resistance to TARSC. Often, a set of these markers will be used, (e.g., 2 or more, 3 or more, 4 or more, 5 or more) in the flanking regions of the locus. Optionally, as described above, a marker flanking or within the actual locus may also be used. The parents and their progeny may be screened for these sets of markers, and the markers that are polymorphic between the two parents used for selection. In an introgression program, this allows for selection of the gene or locus genotype at the more proximal polymorphic markers and selection for the recurrent parent genotype at the more distal polymorphic markers.

The choice of markers actually used to practice the invention is not limited and can be any marker that is genetically linked to the intervals as described herein, which includes markers mapping within the intervals. In certain embodiments, the invention further provides markers closely genetically linked to, or within approximately 0.5 cM of, the markers provided herein and chromosome intervals whose borders fall between or include such markers, and including markers within approximately 0.4 cM, 0.3 cM, 0.2 cM, and about 0.1 cM of the markers provided herein. Examples include any marker selected from SEQ ID NOs: 1, 2, 3, 4, 5, 6, 7, and 36, or markers listed in Tables 5 or 10. Furthermore, since there are many different types of marker detection assays known in the art, it is not intended that the type of marker detection assay used to practice this invention be limited in any way.

Molecular Markers

"Marker," "genetic marker," "molecular marker," "marker nucleic acid," and "marker locus" refer to a nucleotide sequence or encoded product thereof (e.g., a protein) used as a point of reference when identifying a linked locus. A marker can be derived from genomic nucleotide sequence or from expressed nucleotide sequences (e.g., from a spliced RNA, a cDNA, etc.), or from an encoded polypeptide, and can be represented by one or more particular variant sequences, or by a consensus sequence. In another sense, a marker is an isolated variant or consensus of such a sequence. The term also refers to nucleic acid sequences complementary to or flanking the marker sequences, such as nucleic acids used as probes or primer pairs capable of amplifying the marker sequence. A "marker probe" is a nucleic acid sequence or molecule that can be used to identify the presence of a marker locus, e.g., a nucleic acid probe that is complementary to a marker locus sequence. Alternatively, in some aspects, a marker probe refers to a probe of any type that is able to distinguish (i.e., genotype) the particular allele that is present at a marker locus. A "marker locus" is a locus that can be used to track the presence of a second linked locus, e.g., a linked locus that encodes or contributes to expression of a phenotypic trait. For example, a marker locus can be used to monitor segregation of alleles at a locus, such as a QTL, that are genetically or physically linked to the marker locus. Thus, a "marker allele," alternatively an "allele of a marker locus" is one of a plurality of polymorphic nucleotide sequences found at a marker locus in a population that is polymorphic for the marker locus.

"Marker" also refers to nucleic acid sequences complementary to the genomic sequences, such as nucleic acids used as probes. Markers corresponding to genetic polymorphisms between members of a population can be detected by methods well-established in the art. These include, e.g., PCR-based sequence specific amplification methods, detection of restriction fragment length polymorphisms (RFLP), detection of isozyme markers, detection of polynucleotide polymorphisms by allele specific hybridization (ASH), detection of amplified variable sequences of the plant genome, detection of self-sustained sequence replication, detection of simple sequence repeats (SSRs), detection of single nucleotide polymorphisms (SNPs), or detection of amplified fragment length polymorphisms (AFLPs). Well established methods are also know for the detection of expressed sequence tags (ESTs) and SSR markers derived from EST sequences and randomly amplified polymorphic DNA (RAPD).

A favorable allele of a marker is the allele of the marker that co-segregates with a desired phenotype (e.g., disease resistance). As used herein, a QTL marker has a minimum of one favorable allele, although it is possible that the marker might have two or more favorable alleles found in the population. Any favorable allele of that marker can be used advantageously for the identification and construction of disease resistant plant lines. Optionally, one, two, three or more favorable allele(s) of different markers are identified in, or introgressed into a plant, and can be selected for or against during MAS. Desirably, plants or germplasm are identified that have at least one such favorable allele that positively correlates with disease resistance or improved disease resistance. Alternatively, a marker allele that co-segregates with disease susceptibility also finds use with the invention, since that allele can be used to identify and counter select disease susceptible plants. Such an allele can be used for exclusionary purposes during breeding to identify alleles that negatively correlate with resistance, to eliminate susceptible plants or germplasm from subsequent rounds of breeding.

The more tightly linked a marker is with a DNA locus influencing a phenotype, the more reliable the marker is in MAS, as the likelihood of a recombination event unlinking the marker and the locus decreases. Markers containing the causal mutation for a trait, or that are within the coding sequence of a causative gene, are ideal as no recombination is expected between them and the sequence of DNA responsible for the phenotype.

Genetic markers are distinguishable from each other (as well as from the plurality of alleles of any one particular marker) on the basis of polynucleotide length and/or sequence. A large number of corn molecular markers are known in the art, and are published or available from various sources, such as the MaizeGDB internet resource. In general, any differentially inherited polymorphic trait (including a nucleic acid polymorphism) that segregates among progeny is a potential genetic marker.

In some embodiments of the invention, one or more marker alleles are selected for in a single plant or a population of plants. In these methods, plants are selected that contain favorable alleles from more than one resistance marker, or alternatively, favorable alleles from more than one resistance marker are introgressed into a desired germplasm. One of skill recognizes that the identification of favorable marker alleles is germplasm-specific. The determination of which marker alleles correlate with resistance (or susceptibility) is determined for the particular germplasm under study. One of skill recognizes that methods for identifying the favorable alleles are routine and well known in the art, and furthermore, that the identification and use of such favorable alleles is well within the scope of this invention. Furthermore still, identification of favorable marker alleles in plant populations other than the populations used or described herein is well within the scope of this invention.

Marker Detection

In some aspects, methods of the invention utilize an amplification step to detect/genotype a marker locus, but amplification is not always a requirement for marker detection (e.g. Southern blotting and RFLP detection). Separate detection probes can also be omitted in amplification/detection methods, e.g., by performing a real time amplification reaction that detects product formation by modification of the relevant amplification primer upon incorporation into a product, incorporation of labeled nucleotides into an amplicon, or by monitoring changes in molecular rotation properties of amplicons as compared to unamplified precursors (e.g., by fluorescence polarization).

"Amplifying," in the context of nucleic acid amplification, is any process whereby additional copies of a selected nucleic acid (or a transcribed form thereof) are produced. In some embodiments, an amplification-based marker technology is used wherein a primer or amplification primer pair is admixed with genomic nucleic acid isolated from the first plant or germplasm, and wherein the primer or primer pair is complementary or partially complementary to at least a portion of the marker locus, and is capable of initiating DNA polymerization by a DNA polymerase using the plant genomic nucleic acid as a template. The primer or primer pair is extended in a DNA polymerization reaction having a DNA polymerase and a template genomic nucleic acid to generate at least one amplicon. In other embodiments, plant RNA is the template for the amplification reaction. In some embodiments, the QTL marker is a SNP type marker, and the detected allele is a SNP allele, and the method of detection is allele specific hybridization (ASH).

In general, the majority of genetic markers rely on one or more properties of nucleic acids for their detection. Typical amplification methods include various polymerase based replication methods, including the polymerase chain reaction (PCR), ligase mediated methods such as the ligase chain reaction (LCR) and RNA polymerase based amplification (e.g., by transcription) methods. An "amplicon" is an amplified nucleic acid, e.g., a nucleic acid that is produced by amplifying a template nucleic acid by any available amplification method (e.g., PCR, LCR, transcription, or the like). A "genomic nucleic acid" is a nucleic acid that corresponds in sequence to a heritable nucleic acid in a cell. Common examples include nuclear genomic DNA and amplicons thereof. A genomic nucleic acid is, in some cases, different from a spliced RNA, or a corresponding cDNA, in that the spliced RNA or cDNA is processed, e.g., by the splicing machinery, to remove introns. Genomic nucleic acids optionally comprise non-transcribed (e.g., chromosome structural sequences, promoter regions, enhancer regions, etc.) and/or non-translated sequences (e.g., introns), whereas spliced RNA/cDNA typically do not have non-transcribed sequences or introns. A "template nucleic acid" is a nucleic acid that serves as a template in an amplification reaction (e.g., a polymerase based amplification reaction such as PCR, a ligase mediated amplification reaction such as LCR, a transcription reaction, or the like). A template nucleic acid can be genomic in origin, or alternatively, can be derived from expressed sequences, e.g., a cDNA or an EST. Details regarding the use of these and other amplification methods can be found in any of a variety of standard texts. Many available biology texts also have extended discussions regarding PCR and related amplification methods and one of skill will appreciate that essentially any RNA can be converted into a double stranded DNA suitable for restriction digestion, PCR expansion and sequencing using reverse transcriptase and a polymerase.

PCR detection and quantification using dual-labeled fluorogenic oligonucleotide probes, commonly referred to as "TaqMan" probes, can also be performed according to the present invention. These probes are composed of short (e.g., 20-25 base) oligodeoxynucleotides that are labeled with two different fluorescent dyes. On the 5' terminus of each probe is a reporter dye, and on the 3' terminus of each probe a quenching dye is found. The oligonucleotide probe sequence is complementary to an internal target sequence present in a PCR amplicon. When the probe is intact, energy transfer occurs between the two fluorophores and emission from the reporter is quenched by the quencher by FRET. During the extension phase of PCR, the probe is cleaved by 5' nuclease activity of the polymerase used in the reaction, thereby releasing the reporter from the oligonucleotide-quencher and producing an increase in reporter emission intensity. TaqMan™ probes are oligonucleotides that have a label and a quencher, where the label is released during amplification by the exonuclease action of the polymerase used in amplification, providing a real time measure of amplification during synthesis. A variety of TaqMan™ reagents are commercially available, e.g., from Applied Biosystems as well as from a variety of specialty vendors such as Biosearch Technologies.

In one embodiment, the presence or absence of a molecular marker is determined simply through nucleotide sequencing of the polymorphic marker region. This method is readily adapted to high throughput analysis as are the other methods noted above, e.g., using available high throughput sequencing methods such as sequencing by hybridization.

In alternative embodiments, in silico methods can be used to detect the marker loci of interest. For example, the sequence of a nucleic acid comprising the marker locus of interest can be stored in a computer. The desired marker locus sequence or its homolog can be identified using an appropriate nucleic acid search algorithm as provided by, for example, in such readily available programs as the Basic Local Alignment Search Tool (BLAST®), or even simple word processors.

While the exemplary markers provided in the figures and tables herein are either SNP markers, any of the aforementioned marker types can be employed in the context of the invention to identify chromosome intervals encompassing genetic element that contribute to superior agronomic performance (e.g., disease resistance or improved disease tolerance).

Probes and Primers

In general, synthetic methods for making oligonucleotides, including probes, primers, molecular beacons, PNAs, LNAs (locked nucleic acids), etc., are well known. For example, oligonucleotides can be synthesized chemically according to the solid phase phosphoramidite triester method described. Oligonucleotides, including modified oligonucleotides, can also be ordered from a variety of commercial sources.

Nucleic acid probes to the marker loci can be cloned and/or synthesized. Any suitable label can be used with a probe of the invention. Detectable labels suitable for use with nucleic acid probes include, for example, any composition detectable by spectroscopic, radioisotopic, photochemical, biochemical, immunochemical, electrical, optical or chemical means. Useful labels include biotin for staining with labeled streptavidin conjugate, magnetic beads, fluorescent dyes, radio labels, enzymes, and colorimetric labels. Other labels include ligands which bind to antibodies labeled with fluorophores, chemiluminescent agents, and enzymes. A probe can also constitute radio labeled PCR primers that are used to generate a radio labeled amplicon. It is not intended that the nucleic acid probes of the invention be limited to any particular size.

In some embodiments, the molecular markers of the invention are detected using a suitable PCR-based detection method, where the size or sequence of the PCR amplicon is indicative of the absence or presence of the marker (e.g., a particular marker allele). In these types of methods, PCR primers are hybridized to the conserved regions flanking the polymorphic marker region. As used in the art, PCR primers used to amplify a molecular marker are sometimes termed "PCR markers" or simply "markers." It will be appreciated that, although many specific examples of primers are provided herein, suitable primers to be used with the invention can be designed using any suitable method. It is not intended that the invention be limited to any particular primer or primer pair. In some embodiments, the primers of the invention are radiolabelled, or labeled by any suitable means (e.g., using a non-radioactive fluorescent tag), to allow for rapid visualization of the different size amplicons following an amplification reaction without any additional labeling step or visualization step. In some embodiments, the primers are not labeled, and the amplicons are visualized following their size resolution, e.g., following agarose gel electrophoresis. In some embodiments, ethidium bromide staining of the PCR amplicons following size resolution allows visualization of the different size amplicons. It is not intended that the primers of the invention be limited to generating an amplicon of any particular size. For example, the primers used to amplify the marker loci and alleles herein are not limited to amplifying the entire region of the relevant locus. The primers can generate an amplicon of any suitable length that is longer or shorter than those disclosed herein. In some embodiments, marker amplification produces an amplicon at least 20 nucleotides in length, or alternatively, at least 50 nucleotides in length, or alternatively, at least 100 nucleotides in length, or alternatively, at least 200 nucleotides in length. Marker alleles in addition to those recited herein also find use with the present invention.

Linkage Analysis

"Linkage", or "genetic linkage," is used to describe the degree with which one marker locus is associated with another marker locus or some other locus (for example, a resistance locus). A marker locus may be located within a locus to which it is genetically linked. For example, if locus A has genes "A" or "a" and locus B has genes "B" or "b" and a cross between parent 1 with AABB and parent 2 with aabb will produce four possible gametes where the genes are segregated into AB, Ab, aB and ab. The null expectation is that there will be independent equal segregation into each of the four possible genotypes, i.e. with no linkage ¼ of the gametes will of each genotype. Segregation of gametes into a genotypes differing from ¼ is attributed to linkage. As used herein, linkage can be between two markers, or alternatively between a marker and a phenotype. A marker locus may be genetically linked to a trait, and in some cases a marker locus genetically linked to a trait is located within the allele conferring the trait. A marker may also be causative for a trait or phenotype, for example a causative polymorphism. In a further example, a marker locus can be associated with resistance or improved tolerance to a plant pathogen when the marker locus is in linkage disequilibrium with the resistance trait. The degree of linkage of a molecular marker to a phenotypic trait (e.g., a QTL) is measured, e.g., as a statistical probability of co-segregation of that molecular marker with the phenotype.

As used herein, "closely linked" means that the marker or locus is within about 20 cM, for instance within about 10 cM, about 5 cM, about 1 cM, about 0.5 cM, or less than 0.5 cM of the identified locus associated with TARSC resistance.

As used herein, the linkage relationship between a molecular marker and a phenotype is given is the statistical likelihood that the particular combination of a phenotype and the presence or absence of a particular marker allele is random. Thus, the lower the probability score, the greater the likelihood that a phenotype and a particular marker will cosegregate. In some embodiments, a probability score of 0.05 (p=0.05, or a 5% probability) of random assortment is considered a significant indication of co-segregation. However, the present invention is not limited to this particular standard, and an acceptable probability can be any probability of less than 50% (p<0.5). For example, a significant probability can be less than 0.25, less than 0.20, less than 0.15, or less than 0.1. The phrase "closely linked," in the present application, means that recombination between two linked loci occurs with a frequency of equal to or less than about 10% (i.e., are separated on a genetic map by not more than 10 cM). In one aspect, any marker of the invention is linked (genetically and physically) to any other marker that is at or less than 50 cM distant. In another aspect, any marker of the invention is closely linked (genetically and physically) to any other marker that is in close proximity, e.g., at or less than 10 cM distant. Two closely linked markers on the same chromosome can be positioned 9, 8, 7, 6, 5, 4, 3, 2, 1, 0.75, 0.5 or 0.25 cM or less from each other.

Classical linkage analysis can be thought of as a statistical description of the relative frequencies of cosegregation of different traits. Linkage analysis is the well characterized descriptive framework of how traits are grouped together based upon the frequency with which they segregate together. That is, if two non-allelic traits are inherited together with a greater than random frequency, they are said to be "linked." The frequency with which the traits are inherited together is the primary measure of how tightly the traits are linked, i.e., traits which are inherited together with a higher frequency are more closely linked than traits which are inherited together with lower (but still above random) frequency. The further apart on a chromosome the genes reside, the less likely they are to segregate together, because homologous chromosomes recombine during meiosis. Thus, the further apart on a chromosome the genes reside, the more likely it is that there will be a crossing over event during meiosis that will result in the marker and the DNA sequence responsible for the trait the marker is designed to track segregating separately into progeny. A common measure of linkage is the frequency with which traits cosegregate.

Linkage analysis is used to determine which polymorphic marker allele demonstrates a statistical likelihood of co-segregation with the resistance phenotype (thus, a "resistance marker allele"). Following identification of a marker allele for co-segregation with the resistance phenotype, it is possible to use this marker for rapid, accurate screening of plant lines for the resistance allele without the need to grow the plants through their life cycle and await phenotypic evaluations, and furthermore, permits genetic selection for the particular resistance allele even when the molecular identity of the actual resistance QTL is unknown. Tissue samples can be taken, for example, from the endosperm, embryo, or mature/developing plant and screened with the appropriate molecular marker to rapidly determine determined which progeny contain the desired genetics. Linked markers also remove the impact of environmental factors that can often influence phenotypic expression.

Because chromosomal distance is approximately proportional to the frequency of crossing over events between traits, there is an approximate physical distance that correlates with recombination frequency. Marker loci are themselves traits and can be assessed according to standard linkage analysis by tracking the marker loci during segregation. Thus, in the context of the present invention, one cM is equal to a 1% chance that a marker locus will be separated from another locus (which can be any other trait, e.g., another marker locus, or another trait locus that encodes a QTL), due to crossing over in a single generation.

When referring to the relationship between two genetic elements, such as a genetic element contributing to resistance and a proximal marker, "coupling" phase linkage indicates the state where the "favorable" allele at the resistance locus is physically associated on the same chromosome strand as the "favorable" allele of the respective linked marker locus. In coupling phase, both favorable alleles are inherited together by progeny that inherit that chromosome strand. In "repulsion" phase linkage, the "favorable" allele at the locus of interest (e.g., a QTL for resistance) is physically linked with an "unfavorable" allele at the proximal marker locus, and the two "favorable" alleles are not inherited together (i.e., the two loci are "out of phase" with each other).

Genetic Mapping

A "genetic map" is the relationship of genetic linkage among loci on one or more chromosomes (or linkage groups) within a given species, generally depicted in a diagrammatic or tabular form. "Genetic mapping" is the process of defining the linkage relationships of loci through the use of genetic markers, populations segregating for the markers, and standard genetic principles of recombination frequency. A "genetic map location" is a location on a genetic map relative to surrounding genetic markers on the same linkage group where a specified marker can be found within a given species. In contrast, a physical map of the genome refers to absolute distances (for example, measured in base pairs or isolated and overlapping contiguous genetic fragments, e.g., contigs). A physical map of the genome does not take into account the genetic behavior (e.g., recombination frequencies) between different points on the physical map. A "genetic recombination frequency" is the frequency of a crossing over event (recombination) between two genetic loci. Recombination frequency can be observed by following the segregation of markers and/or traits following meiosis. In some cases, two different markers can have the same genetic map coordinates. In that case, the two markers are in such close proximity to each other that recombination occurs between them with such low frequency that it is undetected.

Genetic maps are graphical representations of genomes (or a portion of a genome such as a single chromosome) where the distances between markers are measured by the recombination frequencies between them. Plant breeders use genetic maps of molecular markers to increase breeding efficiency through MAS, a process where selection for a trait of interest is not based on the trait itself but rather on the genotype of a marker linked to the trait. A molecular marker that demonstrates reliable linkage with a phenotypic trait provides a useful tool for indirectly selecting the trait in a plant population, especially when accurate phenotyping is difficult, slow, or expensive.

In general, the closer two markers or genomic loci are on the genetic map, the closer they lie to one another on the physical map. A lack of precise proportionality between cM distances and physical distances can exist due to the fact that the likelihood of genetic recombination is not uniform throughout the genome; some chromosome regions are cross-over "hot spots," while other regions demonstrate only rare recombination events, if any.

Genetic mapping variability can also be observed between different populations of the same crop species. In spite of this variability in the genetic map that may occur between populations, genetic map and marker information derived from one population generally remains useful across multiple populations in identification of plants with desired traits, counter-selection of plants with undesirable traits and in guiding MAS.

As one of skill in the art will recognize, recombination frequencies (and as a result, genetic map positions) in any particular population are not static. The genetic distances separating two markers (or a marker and a QTL) can vary depending on how the map positions are determined. For example, variables such as the parental mapping populations used, the software used in the marker mapping or QTL mapping, and the parameters input by the user of the mapping software can contribute to the QTL marker genetic map relationships. However, it is not intended that the invention be limited to any particular mapping populations, use of any particular software, or any particular set of software parameters to determine linkage of a particular marker or chromosome interval with the disease resistance phenotype. It is well within the ability of one of ordinary skill in the art to extrapolate the novel features described herein to any gene pool or population of interest, and using any particular software and software parameters. Indeed, observations regarding genetic markers and chromosome intervals in populations in addition to those described herein are readily made using the teaching of the present disclosure.

Association Mapping

Association or LD mapping techniques aim to identify genotype-phenotype associations that are significant. It is effective for fine mapping in outcrossing species where frequent recombination among heterozygotes can result in rapid LD decay. LD is non-random association of alleles in a collection of individuals, reflecting the recombinational history of that region. Thus, LD decay averages can help determine the number of markers necessary for a genome-wide association study to generate a genetic map with a desired level of resolution.

Large populations are better for detecting recombination, while older populations are generally associated with higher levels of polymorphism, both of which contribute to accelerated LD decay. However, smaller effective population sizes tend to show slower LD decay, which can result in more extensive haplotype conservation. Understanding of the relationships between polymorphism and recombination is useful in developing strategies for efficiently extracting information from these resources. Association analyses compare the plants' phenotypic score with the genotypes at the various loci. Subsequently, any suitable maize genetic map (for example, a composite map) can be used to help observe distribution of the identified QTL markers and/or QTL marker clustering using previously determined map locations of the markers.

Marker Assisted Selection

"Introgression" refers to the transmission of a desired allele of a genetic locus from one genetic background to another. For example, introgression of a desired allele at a specified locus can be transmitted to at least one progeny via a sexual cross between two parents of the same species, where at least one of the parents has the desired allele in its genome. Alternatively, for example, transmission of an allele can occur by recombination between two donor genomes, e.g., in a fused protoplast, where at least one of the donor protoplasts has the desired allele in its genome. The desired allele can be, e.g., a selected allele of a marker, a QTL, a transgene, or the like. In any case, offspring comprising the desired allele can be repeatedly backcrossed to a line having a desired genetic background and selected for the desired allele, to result in the allele becoming fixed in a selected genetic background.

A primary motivation for development of molecular markers in crop species is the potential for increased efficiency in plant breeding through MAS. Genetic markers are used to identify plants that contain a desired genotype at one or more loci, and that are expected to transfer the desired genotype, along with a desired phenotype to their progeny. Genetic markers can be used to identify plants containing a desired genotype at one locus, or at several unlinked or linked loci (e.g., a haplotype), and that would be expected to transfer the desired genotype, along with a desired phenotype to their progeny. The present invention provides the means to identify plants that are resistant to, exhibit improved resistance to, or are susceptible to TARSC infection by identifying plants having a specified allele that is linked to TARSC-10.01.

In general, MAS uses polymorphic markers that have been identified as having a significant likelihood of co-segregation with a resistance trait. Such markers are presumed to map near a gene or genes that give the plant its resistance phenotype, and are considered indicators for the desired trait, and are termed QTL markers. Plants are tested for the presence or absence of a desired allele in the QTL marker.

Identification of plants or germplasm that include a marker locus or marker loci linked to a resistance trait or traits provides a basis for performing MAS. Plants that comprise favorable markers or favorable alleles are selected for, while plants that comprise markers or alleles that are negatively correlated with resistance can be selected against. Desired markers and/or alleles can be introgressed into plants having a desired (e.g., elite or exotic) genetic background to produce an introgressed resistant plant or germplasm. In some aspects, it is contemplated that a plurality of resistance markers are sequentially or simultaneous selected and/or introgressed. The combinations of resistance markers that are selected for in a single plant is not limited, and can include any combination of markers disclosed herein or any marker linked to the markers disclosed herein, or any markers located within the QTL intervals defined herein.

In some embodiments, a disease resistant first corn plant or germplasm (the donor) can be crossed with a second corn plant or germplasm (the recipient, e.g., an elite or exotic corn, depending on characteristics that are desired in the progeny) to create an introgressed corn plant or germplasm as part of a breeding program designed to improve disease resistance of the recipient corn plant or germplasm. In some aspects, the recipient plant can also contain one or more disease resistant loci, which can be qualitative or quantitative trait loci. In another aspect, the recipient plant can contain a transgene.

In some embodiments, the recipient corn plant or germplasm will typically display reduced resistance to disease conditions as compared to the first corn plant or germplasm, while the introgressed corn plant or germplasm will display an increased resistance to disease conditions as compared to the second plant or germplasm. An introgressed corn plant or germplasm produced by these methods are also a feature of this invention.

MAS is a powerful shortcut to selecting for desired phenotypes and for introgressing desired traits into cultivars (e.g., introgressing desired traits into elite lines). MAS is easily adapted to high throughput molecular analysis methods that can quickly screen large numbers of plant or germplasm genetic material for the markers of interest and is much more cost effective than raising and observing plants for visible traits.

When a population is segregating for multiple loci affecting one of multiple traits, e.g., multiple loci involved in resistance, or multiple loci each involved in resistance or tolerance to different diseases, the efficiency of MAS compared to phenotypic screening becomes even greater, because all of the loci can be evaluated in the lab together from a single sample of DNA.

Introgression of TARSC Resistance Loci Using MAS

The introgression of one or more desired loci from a donor line into another is achieved via repeated backcrossing to a recurrent parent accompanied by selection to retain one or more TARSC resistance loci from the donor parent. Markers associated with TARSC resistance are assayed in progeny and those progeny with one or more TARSC resistance markers are selected for advancement. In another aspect, one or more markers can be assayed in the progeny to select for plants with the genotype of the agronomically elite parent. This invention anticipates that trait introgression activities will require more than one generation, wherein progeny are crossed to the recurrent (agronomically elite) parent or selfed. Selections are made based on the presence of one or more TARSC resistance markers and can also be made based on the recurrent parent genotype, wherein screening is performed on a genetic marker and/or phenotype basis. In another embodiment, markers of this invention can be used in conjunction with other markers, ideally at least one on each chromosome of the corn genome, to track the introgression of TARSC resistance loci into elite germplasm. In another embodiment, QTLs associated with TARSC resistance will be useful in conjunction with SNP molecular markers of the present invention to combine quantitative and qualitative TARSC resistance in the same plant. It is within the scope of this invention to utilize the methods and compositions for trait integration of TARSC resistance. It is contemplated by the inventors that the present invention will be useful for developing commercial varieties with TARSC resistance and an agronomically elite phenotype.

In one aspect, this invention could be used on any plant. In another aspect, the plant is selected from the genus Zea. In another aspect, the plant is selected from the species Zea mays. In a further aspect, the plant is selected from the subspecies Zea mays L. ssp. mays. In an additional aspect, the plant is selected from the group Zea mays L. subsp. mays Indentata, otherwise known as dent corn. In another aspect, the plant is selected from the group Zea mays L. subsp. mays Indurata, otherwise known as flint corn. In an aspect, the plant is selected from the group Zea mays L. subsp. mays Saccharata, otherwise known as sweet corn. In another aspect, the plant is selected from the group Zea mays L. subsp. mays Amylacea, otherwise known as flour corn. In a further aspect, the plant is selected from the group Zea mays L. subsp. mays Everta, otherwise known as pop corn. Zea plants include hybrids, inbreds, partial inbreds, or members of defined or undefined populations.

In another aspect, a corn plant of the invention can show a comparative resistance compared to a non-resistant control corn plant. In this aspect, a control corn plant will preferably be genetically similar except for the disease resistance allele or alleles in question. Such plants can be grown under similar conditions with equivalent or near equivalent exposure to the pathogen.

Transgenic Plants

Embodiments of the invention further provide transgenic plants transformed with DNA sequences derived from the novel chromosome intervals identified herein. For example, one or more subregions, fragments, or coding sequences within the TARSC-10.01 interval or other intervals associated with TARSC resistance provided herein may be transformed into a plant. Vectors used for plant transformation may include, for example, plasmids, cosmids, YACs (yeast artificial chromosomes), BACs (bacterial artificial chromosomes) or any other suitable cloning system, as well as fragments of DNA therefrom. Thus when the term "vector" or "expression vector" is used, all of the foregoing types of vectors, as well as nucleic acid sequences isolated therefrom, are included. It is contemplated that utilization of cloning systems with large insert capacities will allow introduction of large DNA sequences comprising more than one selected gene. In accordance with the present disclosure, this could be used to introduce multiple genetic loci or genes associated with TARSC resistance into a plant.

Particularly useful for transformation are expression cassettes comprising a DNA sequence to be introduced into a plant or plant cell. DNA segments used for transforming plant cells will generally comprise a cDNA, gene, or genes which one desires to introduce into and have expressed in the host cells. These DNA segments can further include structures such as promoters, enhancers, polylinkers, or regulatory genes as desired. The DNA segment or gene chosen for cellular introduction will often encode a protein which will be expressed in the resultant recombinant cells resulting in a screenable or selectable trait and/or which will impart an improved phenotype to the resulting transgenic plant.

Regulatory elements such as promoters, leaders, enhancers, introns, and transcription termination regions (or 3' UTRs) can play an integral part in the overall expression of genes in living cells. The term "regulatory element," as used herein, refers to a DNA molecule having gene-regulatory activity. The term "gene-regulatory activity," as used herein, refers to the ability to affect the expression of an operably linked transcribable DNA molecule, for instance by affecting the transcription and/or translation of the operably linked transcribable DNA molecule. Regulatory elements, such as promoters, leaders, enhancers, and introns that function in plants are therefore useful for modifying plant phenotypes through genetic engineering.

As used herein, the term "intron" refers to a DNA molecule that may be isolated or identified from the genomic copy of a gene and may be defined generally as a region spliced out during messenger RNA (mRNA) processing prior to translation. Alternately, an intron may be a synthetically produced or manipulated DNA element. An intron may contain enhancer elements that effect the transcription of operably linked genes. An intron may be used as a regulatory element for modulating expression of an operably linked transcribable DNA molecule. A construct may comprise an intron, and the intron may or may not be heterologous with respect to the transcribable DNA molecule. Examples of introns in the art include the rice actin intron and the corn HSP70 intron. In plants, the inclusion of some introns in constructs leads to increased mRNA and protein accumulation relative to constructs lacking the intron. This effect has been termed "intron mediated enhancement" (IME) of gene expression. Introns known to stimulate expression in plants have been identified in maize genes (e.g., tubA1, Adh1, Sh1, and Ubi1), in rice genes (e.g., tpi) and in dicotyledonous plant genes like those from *petunia* (e.g., rbcS), potato (e.g., st-ls1) and from *Arabidopsis thaliana* (e.g., ubq3 and pat1).

As used herein, the term "enhancer" or "enhancer element" refers to a cis-acting regulatory element, a.k.a. cis-element, which confers an aspect of the overall expression pattern, but is usually insufficient alone to drive transcription, of an operably linked DNA sequence. Unlike promoters, enhancer elements do not usually include a transcription start site (TSS) or TATA box or equivalent DNA sequence. A promoter or promoter fragment may naturally comprise one or more enhancer elements that affect the transcription of an operably linked DNA sequence. An enhancer element may also be fused to a promoter to produce a chimeric promoter cis-element, which confers an aspect of the overall modulation of gene expression.

Regulatory elements may be characterized by their gene expression pattern, e.g., positive and/or negative effects, such as constitutive expression or temporal, spatial, developmental, tissue, environmental, physiological, pathological, cell cycle, and/or chemically responsive expression, and any combination thereof, as well as by quantitative or qualitative indications. As used herein, a "gene expression pattern" is any pattern of transcription of an operably linked DNA molecule into a transcribed RNA molecule. The transcribed RNA molecule may be translated to produce a protein molecule or may provide an antisense or other regulatory RNA molecule, such as a double-stranded RNA (dsRNA), a transfer RNA (tRNA), a ribosomal RNA (rRNA), a microRNA (miRNA), and the like.

As used herein, the term "protein expression" is any pattern of translation of a transcribed RNA molecule into a protein molecule. Protein expression may be characterized by its temporal, spatial, developmental, or morphological qualities, as well as by quantitative or qualitative indications.

A promoter is useful as a regulatory element for modulating the expression of an operably linked transcribable DNA molecule. As used herein, the term "promoter" refers generally to a DNA molecule that is involved in recognition and binding of RNA polymerase II and other proteins, such as trans-acting transcription factors, to initiate transcription. A promoter may originate from the 5' untranslated region (5' UTR) of a gene. Alternately, promoters may be synthetically produced or manipulated DNA molecules. Promoters may also be chimeric.

The DNA sequence between the transcription initiation site and the start of the coding sequence, i.e., the untranslated leader sequence, can also influence gene expression. As used herein, the term "leader" refers to a DNA molecule from the untranslated 5' region (5' UTR) of a gene and defined generally as a DNA segment between the transcription start site (TSS) and the protein coding sequence start site. Alternately, leaders may be synthetically produced or manipulated DNA elements. A leader can be used as a 5' regulatory element for modulating expression of an operably linked transcribable DNA molecule. Leader molecules may be used with a heterologous promoter or with their native promoter. One may thus wish to employ a particular leader sequence with a transformation construct of the present disclosure.

Transformation constructs prepared in accordance with the present disclosure may further include a 3' end DNA sequence that acts as a signal to terminate transcription and allow for the polyadenylation of the mRNA produced by coding sequences operably linked to a promoter. As used herein, the term "3' transcription termination molecule," "3' untranslated region" or "3' UTR" herein refers to a DNA molecule that is used during transcription to the untranslated region of the 3' portion of an mRNA molecule. The 3' untranslated region of an mRNA molecule may be generated by specific cleavage and 3' polyadenylation, also known as a polyA tail. A 3' UTR may be operably linked to and located downstream of a transcribable DNA molecule and may include a polyadenylation signal and other regulatory signals capable of affecting transcription, mRNA processing, or gene expression. PolyA tails are thought to function in mRNA stability and in initiation of translation. Examples of 3' transcription termination molecules in the art are the nopaline synthase 3' region; wheat hsp17 3' region, pea rubisco small subunit 3' region, cotton E6 3' region, and the coixin 3' UTR.

Additionally, vectors may be constructed and employed in the intracellular targeting of a specific gene product within the cells of a transgenic plant or in directing a protein to the extracellular environment. This generally will be achieved by joining a DNA sequence encoding a transit or signal peptide sequence to the coding sequence of a particular gene. The resultant transit or signal peptide will transport the protein to a particular intracellular or extracellular destination, respectively, and will then be post-translationally removed.

By employing a selectable or screenable marker, one can provide or enhance the ability to identify transformants. "Marker genes" are genes that impart a distinct phenotype to cells expressing the marker protein and thus allow such transformed cells to be distinguished from cells that do not have the marker. Such genes may encode either a selectable or screenable marker, depending on whether the marker confers a trait which one can "select" for by chemical means, i.e., through the use of a selective agent (e.g., a herbicide, antibiotic, or the like), or whether it is simply a trait that one can identify through observation or testing, i.e., by "screening" (e.g., the green fluorescent protein). Of course, many examples of suitable marker proteins are known to the art and can be employed in the practice of the present disclosure.

Selectable marker transgenes may also be used with the present disclosure. As used herein the term "selectable marker transgene" refers to any transcribable DNA molecule whose expression in a transgenic plant, tissue or cell, or lack thereof, can be screened for or scored in some way. Selectable marker genes, and their associated selection and screening techniques, for use in the practice of the present disclosure are known in the art and include, but are not limited to, transcribable DNA molecules encoding β-glucuronidase (GUS), green fluorescent protein (GFP), proteins that confer antibiotic resistance, and proteins that confer herbicide resistance.

Plant Cell Transformation Methods

Numerous methods for transforming chromosomes in a plant cell with recombinant DNA are known in the art and are used in methods of producing a transgenic plant cell and plant. Two effective methods for such transformation are *Agrobacterium*-mediated transformation and microprojectile bombardment-mediated transformation. Microprojectile bombardment methods are illustrated, for example, in U.S. Pat. No. 5,550,318; U.S. Pat. No. 5,538,880; U.S. Pat. No. 6,160,208; and U.S. Pat. No. 6,399,861. *Agrobacterium*-mediated transformation methods are described, for example in U.S. Pat. No. 5,591,616, which is incorporated herein by reference in its entirety. Transformation of plant material is practiced in tissue culture on nutrient media, for example a mixture of nutrients that allow cells to grow in vitro. Recipient cell targets include, but are not limited to, meristem cells, shoot tips, hypocotyls, calli, immature or mature embryos, and gametic cells such as microspores and pollen. Callus can be initiated from tissue sources including, but not limited to, immature or mature embryos, hypocotyls, seedling apical meristems, microspores and the like. Cells containing a transgenic nucleus are grown into transgenic plants.

In addition to direct transformation of a plant material with a recombinant DNA, a transgenic plant can be prepared by crossing a first plant comprising a recombinant DNA with a second plant lacking the recombinant DNA. For example, recombinant DNA can be introduced into a first plant line that is amenable to transformation, which can be crossed with a second plant line to introgress the recombinant DNA into the second plant line. A transgenic plant with recombinant DNA providing an enhanced trait, for example, enhanced yield, can be crossed with a transgenic plant line having another recombinant DNA that confers another trait, for example herbicide resistance or pest resistance or enhanced water use efficiency, to produce progeny plants having recombinant DNA that confers both traits. Typically, in such breeding for combining traits the transgenic plant donating the additional trait is the male line and the transgenic plant carrying the base traits is the female line. The progeny of this cross will segregate such that some of the plants will carry the DNA for both parental traits and some will carry DNA for one parental trait; such plants can be identified by markers associated with parental recombinant DNA, for example, marker identification by analysis for recombinant DNA or, in the case where a selectable marker is linked to the recombinant DNA, by application using a selective agent such as a herbicide for use with a herbicide resistance marker, or by selection for the enhanced trait. Progeny plants carrying DNA for both parental traits can be crossed back into the female parent line multiple times, for example usually 6 to 8 generations, to produce a progeny plant with substantially the same genotype as the original transgenic parental line but for the recombinant DNA of the other transgenic parental line.

In transformation, DNA is typically introduced into only a small percentage of target plant cells in any one transformation experiment. Marker genes are used to provide an efficient system for identification of those cells that are stably transformed by receiving and integrating a recombinant DNA molecule into their genomes. Preferred marker genes provide selective markers which confer resistance to a selective agent, such as an antibiotic or an herbicide. Any of the herbicides to which plants of this disclosure can be resistant is an agent for selective markers. Potentially transformed cells are exposed to the selective agent. In the population of surviving cells are those cells where, generally, the resistance-conferring gene is integrated and expressed at sufficient levels to permit cell survival. Cells can be tested further to confirm stable integration of the exogenous DNA. Commonly used selective marker genes include those conferring resistance to antibiotics such as kanamycin and paromomycin (nptII), hygromycin B (aph IV), spectinomycin (aadA) and gentamycin (aac3 and aacC4) or resistance to herbicides such as glufosinate (bar or pat), dicamba (DMO) and glyphosate (aroA or EPSPS). Examples of such selectable markers are illustrated in U.S. Pat. No. 5,550,318; U.S. Pat. No. 5,633,435; U.S. Pat. No. 5,780,708 and U.S. Pat. No. 6,118,047. Markers which provide an ability to visually screen transformants can also be employed, for example, a gene expressing a colored or fluorescent protein such as a luciferase or green fluorescent protein (GFP) or a gene expressing a beta-glucuronidase or uidA gene (GUS) for which various chromogenic substrates are known.

Transgenic Plants and Seeds

Transgenic plants derived from transgenic plant cells may be grown to generate transgenic plants having an enhanced trait as compared to a control plant, and produce transgenic seed and haploid pollen of this disclosure. Such plants with enhanced traits are identified by selection of transformed plants or progeny seed for the enhanced trait. For efficiency, a selection method is designed to evaluate multiple transgenic plants (events) comprising the recombinant DNA, for example multiple plants from 2 to 20 or more transgenic events. Transgenic plants grown from transgenic seeds provided herein demonstrate improved agronomic traits, such as resistance to TARSC in maize.

Definitions

The definitions and methods provided define the present invention and guide those of ordinary skill in the art in the practice of the present invention. Unless otherwise noted, terms are to be understood according to conventional usage by those of ordinary skill in the relevant art. Examples of resources describing many of the terms related to molecular biology used herein can be found in in Alberts et al., Molecular Biology of The Cell, 5$^{th}$ Edition, Garland Science Publishing, Inc.: New York, 2007; Rieger et al., Glossary of Genetics: Classical and Molecular, 5th edition, Springer-Verlag: New York, 1991; King et al, A Dictionary of Genetics, 6th ed., Oxford University Press: New York, 2002; and Lewin, Genes Icorn, Oxford University Press: New York, 2007. The nomenclature for DNA bases as set forth at 37 CFR § 1.822 is used.

"Adjacent", when used to describe a nucleic acid molecule that hybridizes to DNA containing a polymorphism, refers to a nucleic acid that hybridizes to DNA sequences that directly abut the polymorphic nucleotide base position. For example, a nucleic acid molecule that can be used in a single base extension assay is "adjacent" to the polymorphism.

"Allele" refers to an alternative nucleic acid sequence at a particular locus; the length of an allele can be as small as 1 nucleotide base, but is typically larger. For example, a first allele can occur on one chromosome, while a second allele occurs on a second homologous chromosome, e.g., as occurs for different chromosomes of a heterozygous individual, or between different homozygous or heterozygous individuals in a population. A favorable allele is the allele at a particular locus that confers, or contributes to, an agronomically desirable phenotype, or alternatively, is an allele that allows the identification of susceptible plants that can be removed from a breeding program or planting. A favorable allele of a marker is a marker allele that segregates with the favorable phenotype, or alternatively, segregates with susceptible plant phenotype, therefore providing the benefit of identifying disease prone plants. A favorable allelic form of a chromosome interval is a chromosome interval that includes a nucleotide sequence that contributes to superior agronomic performance at one or more genetic loci physically located on the chromosome interval. "Allele frequency" refers to the frequency (proportion or percentage) at which an allele is present at a locus within an individual, within a line, or within a population of lines. For example, for an allele "A," diploid individuals of genotype "AA," "Aa," or "aa" have allele frequencies of 1.0, 0.5, or 0.0, respectively. One can estimate the allele frequency within a line by averaging the allele frequencies of a sample of individuals from that line. Similarly, one can calculate the allele frequency within a population of lines by averaging the allele frequencies of lines that make up the population. For a population with a finite number of individuals or lines, an allele frequency can be expressed as a count of individuals or lines (or any other specified grouping) containing the allele. An allele positively correlates with a trait when it is linked to it and when presence of the allele is an indictor that the desired trait or trait form will occur in a plant comprising the allele. An allele negatively correlates with a trait when it is linked to it and when presence of the allele is an indicator that a desired trait or trait form will not occur in a plant comprising the allele.

"Crossed" or "cross" means to produce progeny via fertilization (e.g. cells, seeds or plants) and includes crosses between plants (sexual) and self fertilization (selfing).

"Elite line" means any line that has resulted from breeding and selection for superior agronomic performance. Numerous elite lines are available and known to those of skill in the art of corn breeding. An "elite population" is an assortment of elite individuals or lines that can be used to represent the state of the art in terms of agronomically superior genotypes of a given crop species, such as corn. Similarly, an "elite germplasm" or elite strain of germplasm is an agronomically superior germplasm.

"Exogenous nucleic acid" is a nucleic acid that is not native to a specified system (e.g., a germplasm, plant, variety, etc.), with respect to sequence, genomic position, or both. As used herein, the terms "exogenous" or "heterologous" as applied to polynucleotides or polypeptides typically refers to molecules that have been artificially supplied to a biological system (e.g., a plant cell, a plant gene, a particular plant species or variety or a plant chromosome under study) and are not native to that particular biological system. The terms can indicate that the relevant material originated from a source other than a naturally occurring source, or can refer to molecules having a non-natural configuration, genetic location or arrangement of parts. In contrast, for example, a "native" or "endogenous" gene is a gene that does not contain nucleic acid elements encoded by sources other than the chromosome or other genetic element on which it is normally found in nature. An endogenous gene, transcript or polypeptide is encoded by its natural chromosomal locus, and not artificially supplied to the cell.

"Genetic element" or "gene" refers to a heritable sequence of DNA, i.e., a genomic sequence, with functional significance. The term "gene" can also be used to refer to, e.g., a cDNA and/or an mRNA encoded by a genomic sequence, as well as to that genomic sequence.

"Genotype" is the genetic constitution of an individual (or group of individuals) at one or more genetic loci, as contrasted with the observable trait (the phenotype). Genotype is defined by the allele(s) of one or more known loci that the individual has inherited from its parents. The term genotype can be used to refer to an individual's genetic constitution at a single locus, at multiple loci, or, more generally, the term genotype can be used to refer to an individual's genetic make-up for all the genes in its genome. A "haplotype" is the genotype of an individual at a plurality of genetic loci. Typically, the genetic loci described by a haplotype are physically and genetically linked, i.e., on the same chromosome interval. The terms "phenotype," or "phenotypic trait" or "trait" refers to one or more trait of an organism. The phenotype can be observable to the naked eye, or by any other means of evaluation known in the art, e.g., microscopy, biochemical analysis, genomic analysis, an assay for a particular disease resistance, etc. In some cases, a phenotype is directly controlled by a single gene or genetic locus, i.e., a "single gene trait." In other cases, a phenotype is the result of several genes.

"Germplasm" refers to genetic material of or from an individual (e.g., a plant), a group of individuals (e.g., a plant line, variety or family), or a clone derived from a line, variety, species, or culture. The germplasm can be part of an organism or cell, or can be separate from the organism or cell. In general, germplasm provides genetic material with a specific molecular makeup that provides a physical foundation for some or all of the hereditary qualities of an organism or cell culture. As used herein, germplasm includes cells, seed or tissues from which new plants may be grown, or plant parts, such as leaves, stems, pollen, or cells that can be cultured into a whole plant.

"Linkage disequilibrium" refers to a non-random segregation of genetic loci or traits (or both). In either case, linkage disequilibrium implies that the relevant loci are within sufficient physical proximity along a length of a chromosome so that they segregate together with greater than random (i.e., non-random) frequency (in the case of co-segregating traits, the loci that underlie the traits are in sufficient proximity to each other). Linked loci co-segregate more than 50% of the time, e.g., from about 51% to about 100% of the time. The term "physically linked" is sometimes used to indicate that two loci, e.g., two marker loci, are physically present on the same chromosome. Advantageously, the two linked loci are located in close proximity such that recombination between homologous chromosome pairs does not occur between the two loci during meiosis with high frequency, e.g., such that linked loci cosegregate at least about 90% of the time, e.g., 91%, 92%, 93%, 94%, 95%, 96%, 97%, 98%, 99%, 99.5%, 99.75%, or more of the time.

"Locus" a chromosome region where a polymorphic nucleic acid, trait determinant, gene or marker is located. The loci of this invention comprise one or more polymorphisms in a population; i.e., alternative alleles are present in some individuals. A "gene locus" is a specific chromosome location in the genome of a species where a specific gene can be found.

"Marker Assay" means a method for detecting a polymorphism at a particular locus using a particular method, e.g. measurement of at least one phenotype (such as seed color, flower color, or other visually detectable trait), restriction fragment length polymorphism (RFLP), single base extension, electrophoresis, sequence alignment, allelic specific oligonucleotide hybridization (ASO), random amplified polymorphic DNA (RAPD), microarray-based technologies, and nucleic acid sequencing technologies, etc. "Marker Assisted Selection" (MAS) is a process by which phenotypes are selected based on marker genotypes.

"Molecular phenotype" is a phenotype detectable at the level of a population of one or more molecules. Such molecules can be nucleic acids, proteins, or metabolites. A molecular phenotype could be an expression profile for one or more gene products, e.g., at a specific stage of plant development, in response to an environmental condition or stress, etc.

"Operably linked" refers to the association of two or more nucleic acid elements in a recombinant DNA construct, e.g. as when a promoter is operably linked with DNA that is transcribed to RNA whether for expressing or suppressing a protein. Recombinant DNA constructs can be designed to express a protein which can be an endogenous protein, an exogenous homologue of an endogenous protein or an exogenous protein with no native homologue. Alternatively, recombinant DNA constructs can be designed to suppress the level of an endogenous protein, e.g. by suppression of the native gene. Such gene suppression can be effectively employed through a native RNA interference (RNAi) mechanism in which recombinant DNA comprises both sense and anti-sense oriented DNA matched to the gene targeted for suppression where the recombinant DNA is transcribed into RNA that can form a double-strand to initiate an RNAi mechanism. Gene suppression can also be effected by recombinant DNA that comprises anti-sense oriented DNA matched to the gene targeted for suppression. Gene suppression can also be effected by recombinant DNA that comprises DNA that is transcribed to a microRNA matched to the gene targeted for suppression.

"Percent identity" or "% identity" means the extent to which two optimally aligned DNA or protein segments are invariant throughout a window of alignment of components, for example nucleotide sequence or amino acid sequence. An "identity fraction" for aligned segments of a test sequence and a reference sequence is the number of identical components that are shared by sequences of the two aligned segments divided by the total number of sequence components in the reference segment over a window of alignment which is the smaller of the full test sequence or the full reference sequence.

"Phenotype" means the detectable characteristics of a cell or organism which can be influenced by genotype.

"Plant" refers to a whole plant any part thereof, or a cell or tissue culture derived from a plant, comprising any of: whole plants, plant components or organs (e.g., leaves, stems, roots, etc.), plant tissues, seeds, plant cells, and/or progeny of the same. A plant cell is a biological cell of a plant, taken from a plant or derived through culture from a cell taken from a plant.

"Polymorphism" means the presence of one or more variations in a population. A polymorphism may manifest as a variation in the nucleotide sequence of a nucleic acid or as a variation in the amino acid sequence of a protein. Polymorphisms include the presence of one or more variations of a nucleic acid sequence or nucleic acid feature at one or more loci in a population of one or more individuals. The variation may comprise but is not limited to one or more nucleotide base changes, the insertion of one or more nucleotides or the deletion of one or more nucleotides. A polymorphism may arise from random processes in nucleic acid replication, through mutagenesis, as a result of mobile genomic elements, from copy number variation and during the process of meiosis, such as unequal crossing over, genome duplication and chromosome breaks and fusions. The variation can be commonly found or may exist at low frequency within a population, the former having greater utility in general plant breeding and the latter may be associated with rare but important phenotypic variation. Useful polymorphisms may include single nucleotide polymorphisms (SNPs), insertions or deletions in DNA sequence (Indels), simple sequence repeats of DNA sequence (SSRs), a restriction fragment length polymorphism, and a tag SNP. A genetic marker, a gene, a DNA-derived sequence, a RNA-derived sequence, a promoter, a 5' untranslated region of a gene, a 3' untranslated region of a gene, microRNA, siRNA, a resistance locus, a satellite marker, a transgene, mRNA, ds mRNA, a transcriptional profile, and a methylation pattern may also comprise polymorphisms. In addition, the presence, absence, or variation in copy number of the preceding may comprise polymorphisms.

A "population of plants" or "plant population" means a set comprising any number, including one, of individuals, objects, or data from which samples are taken for evaluation, e.g. estimating QTL effects. Most commonly, the terms relate to a breeding population of plants from which members are selected and crossed to produce progeny in a breeding program. A population of plants can include the progeny of a single breeding cross or a plurality of breeding crosses, and can be either actual plants or plant derived material, or in silico representations of the plants. The population members need not be identical to the population members selected for use in subsequent cycles of analyses or those ultimately selected to obtain final progeny plants. Often, a plant population is derived from a single biparental cross, but may also derive from two or more crosses between the same or different parents. Although a population of plants may comprise any number of individuals, those of skill in the art will recognize that plant breeders commonly use population sizes ranging from one or two hundred individuals to several thousand, and that the highest performing 5-20% of a population is what is commonly selected to be used in subsequent crosses in order to improve the performance of subsequent generations of the population.

"Resistance" or "improved resistance" in a plant to disease conditions is an indication that the plant is more able to reduce disease burden than a non-resistant or less resistant plant. Resistance is a relative term, indicating that a "resistant" plant is more able to reduce disease burden compared to a different (less resistant) plant (e.g., a different corn line) grown in similar disease conditions. One of skill will appreciate that plant resistance to disease conditions varies widely, and can represent a spectrum of more-resistant or less-resistant phenotypes. However, by simple observation, one of skill can generally determine the relative resistance of different plants, plant lines, or plant families under disease conditions, and furthermore, will also recognize the phenotypic gradations of "resistant."

"Resistance locus" means a locus that contributes resistance, tolerance, or susceptibility to TARSC.

"Resistance allele" means the nucleic acid sequence associated with resistance or tolerance to disease.

"Tolerance locus" means a locus associated with tolerance or resistance to disease. For instance, a tolerance locus according to the present invention may, in one embodiment, control tolerance or susceptibility for TARSC.

"Tolerance allele" means the nucleic acid sequence associated with tolerance or resistance to disease.

"Recombinant" in reference to a nucleic acid or polypeptide indicates that the material (e.g., a recombinant nucleic acid, gene, polynucleotide, polypeptide, etc.) has been altered by human intervention. The term recombinant can also refer to an organism that harbors recombinant material, e.g., a plant that comprises a recombinant nucleic acid is considered a recombinant plant.

"Tolerance" or "improved tolerance" in a plant to disease conditions is an indication that the plant is less affected by disease conditions with respect to yield, survivability and/or other relevant agronomic measures, compared to a less resistant, more "susceptible" plant. Tolerance is a relative term, indicating that a "tolerant" plant survives and/or produces better yields in disease conditions compared to a different (less tolerant) plant (e.g., a different corn line strain) grown in similar disease conditions. One of skill will appreciate that plant tolerance to disease conditions varies widely, and can represent a spectrum of more-tolerant or less-tolerant phenotypes. However, by simple observation, one of skill can generally determine the relative tolerance or susceptibility of different plants, plant lines or plant families under disease conditions, and furthermore, will also recognize the phenotypic gradations of "tolerant."

"Transgenic plant" refers to a plant that comprises within its cells a heterologous polynucleotide. Generally, the heterologous polynucleotide is stably integrated within the genome such that the polynucleotide is passed on to successive generations. The heterologous polynucleotide may be integrated into the genome alone or as part of a recombinant expression cassette. "Transgenic" is used herein to refer to any cell, cell line, callus, tissue, plant part or plant, the genotype of which has been altered by the presence of heterologous nucleic acid including those transgenic organisms or cells initially so altered, as well as those created by crosses or asexual propagation from the initial transgenic organism or cell. The term "transgenic" as used herein does not encompass the alteration of the genome (chromosomal or extrachromosomal) by conventional plant breeding methods (e.g., crosses) or by naturally occurring events such as random cross-fertilization, non-recombinant viral infection, non-recombinant bacterial transformation, non-recombinant transposition, or spontaneous mutation.

"Vector" is a polynucleotide or other molecule that transfers nucleic acids between cells. Vectors are often derived from plasmids, bacteriophages, or viruses and optionally comprise parts which mediate vector maintenance and enable its intended use. A "cloning vector" or "shuttle vector" or "subcloning vector" contains operably linked parts that facilitate subcloning steps (e.g., a multiple cloning site containing multiple restriction endonuclease sites). The term "expression vector" as used herein refers to a vector comprising operably linked polynucleotide sequences that facilitate expression of a coding sequence in a particular host organism (e.g., a bacterial expression vector or a plant expression vector).

"Yield" is the culmination of all agronomic traits as determined by the productivity per unit area of a particular plant product of commercial value. "Agronomic traits," include the underlying genetic elements of a given plant variety that contribute to yield over the course of growing season.

EXAMPLES

Example 1. Identification of TARSC-10.01

TARSC disease resistance was measured by rating the percentage of leaf area infected on a scale of 1 (very resistant) to 9 (susceptible) as shown in Table 1. Individual plant scores from rows of 20 plants each were averaged and reported as a final score for the row.

TABLE 1

Description of TARSC rating scale.

| Symptoms | Score | Rating |
| --- | --- | --- |
| 0% of leaf area infected; no visible lesions | 1 | Very Resistant |
| ILA < 1%; few lesions, dispersed through lower leaves | 2 | Very Resistant |
| 1% ≤ ILA < 20% | 3 | Resistant |
| 20% ≤ ILA < 40% | 4 | Resistant |
| 40% ≤ ILA < 50%; lesions reaching ear leaf, with sparse lesions in the leaves above the ear | 5 | Mid-Resistant |
| 50% ≤ ILA < 60%; lesions reaching the leaves above the ear | 6 | Mid-Susceptible |
| 60% ≤ ILA < 75% | 7 | Susceptible |
| 75% ≤ ILA < 90% | 8 | Susceptible |
| >90% of foliar area infected, with premature death of the plant before forming black layer | 9 | Susceptible |

ILA = infected leaf area.

Parental lines were selected from resistant inbred line CV001735, and susceptible inbred lines CV001988, CV004552, CV004755 and CV774864. CV774864 is described in U.S. Pat. No. 8,367,906 issued on Feb. 5, 2013, which is incorporated herein in its entirety. The average TARSC rating score was 1 for CV001735, 8 for CV001988, 7 for CV004552, and 8 for CV004755 and CV774864. Doubled-haploid plants were derived from CV001735/CV001988*2 BC1F1, CV004552*2/CV001735 BC1F1, CV004755*2/CV001735 BC1F1 and F3 inbred plants were derived from CV001735/CV774864 (Table 2).

TABLE 2

Bi-parental mapping populations.

| Mapping Population | Cross | Resistant Line | Susceptible Line | Population Type |
| --- | --- | --- | --- | --- |
| A | CV001735/CV001988*2 | CV001735 | CV001988 | DH BC1F1 |
| B | CV004552*2/CV001735 | CV001735 | CV004552 | DH BC1F1 |
| C | CV004755*2/CV001735 | CV001735 | CV004755 | DH BC1F1 |
| D | CV001735/CV774864 | CV001735 | CV774864 | F3 |

In order to detect QTLs associated with TARSC resistance, plants were grown under natural disease infection at well-selected locations based on observations of disease pressure. Each mapping population was measured for TARSC resistance in two field replicates and the basic statistics are shown in Table 3.

TABLE 3

Basic statistics for each mapping population.

| Mapping Population | Replicate ID | Mean TARSC score | Number of Lines | Standard Deviation | Variance | Coefficient of Variation |
| --- | --- | --- | --- | --- | --- | --- |
| A | combined | 6.4 | 436 | 2.5 | 6.3 | 39.4 |
|  | 1 | 6.3 | 217 | 2.4 | 5.9 | 38.5 |
|  | 2 | 6.4 | 219 | 2.6 | 6.7 | 40.3 |

TABLE 3-continued

Basic statistics for each mapping population.

| Mapping Population | Replicate ID | Mean TARSC score | Number of Lines | Standard Deviation | Variance | Coefficient of Variation |
|---|---|---|---|---|---|---|
| B | combined | 4.2 | 449 | 2.2 | 4.8 | 51.7 |
|   | 1 | 4.1 | 225 | 2.1 | 4.3 | 51.3 |
|   | 2 | 4.4 | 224 | 2.3 | 5.2 | 52 |
| C | combined | 5 | 439 | 2.4 | 5.7 | 48.1 |
|   | 1 | 5.2 | 219 | 2.4 | 5.6 | 45.9 |
|   | 2 | 4.8 | 220 | 2.4 | 5.8 | 50.2 |
| D | combined | 2.8 | 399 | 1.3 | 1.8 | 47.9 |
|   | 1 | 2.8 | 199 | 1.4 | 1.8 | 48.7 |
|   | 2 | 2.8 | 200 | 1.3 | 1.8 | 47.4 |

A standard statistical model was run to estimate the variance components and to compute the heritability ($H^2$) for TARSC phenotype (Table 4).

TABLE 4

Variance component estimation and heritability analysis.

| Mapping Population | Genetic variance | Residue variance | Total phenotypic variance | $H^2$ |
|---|---|---|---|---|
| A | 5.67 | 0.56 | 6.23 | 0.9 |
| B | 4.3 | 0.46 | 4.76 | 0.9 |
| C | 5.12 | 0.6 | 5.72 | 0.9 |
| D | 0.63 | 0.99 | 1.6 | 0.4 |

Plants from all mapping populations were then genotyped using SNP markers that collectively spanned each chromosome in the maize genome. The primer sequences for amplifying exemplary SNP marker loci linked to the TARSC and the probes used to genotype the corresponding SNP sequences are provided in Table 5. One of skill in the art will recognize that sequences to either side of the given primers can be used in place of the given primers, so long as the primers can amplify a region that includes the allele to be detected. The precise probe used for detection can vary, e.g., any probe that can identify the region of a marker amplicon to be detected can be substituted for those probes exemplified herein. Configuration of the amplification primers and detection probes can also be varied. Thus, the invention is not limited to the primers, probes, or marker sequences specifically recited herein.

TABLE 5

SNP markers associated with TARSC resistance.

| | | SEQ ID NO. | | | |
|---|---|---|---|---|---|
| SEQ ID NO. | SNP Position | Fwd Primer | Rev Primer | Probe 1 | Probe 2 |
| 1 | 61 | 8 | 15 | 22 | 29 |
| 2 | 61 | 9 | 16 | 23 | 30 |
| 3 | 132 | 10 | 17 | 24 | 31 |
| 4 | 61 | 11 | 18 | 25 | 32 |
| 5 | 101 | 12 | 19 | 26 | 33 |
| 6 | 61 | 13 | 20 | 27 | 34 |
| 7 | 101 | 14 | 21 | 28 | 35 |

In an illustrative example, SNP marker SEQ ID NO: 1 can be amplified using the primers described in Table 5 as SEQ ID NO: 8 (forward primer) and SEQ ID NO: 15 (reverse primer), and detected with probes indicated as SEQ ID NO: 22 (Probe 1) and SEQ ID NO: 29 (Probe 2).

Marker-trait association studies were performed using both single-marker analysis (SMA) and composite interval mapping (CIM). For each marker, the thresholds of likelihood ratio between full and null models for CIM were based on 1000 random permutation tests and the thresholds (p-value) for SMA were based on 10,000 random permutation tests (Churchill and Doerg, 1994).

The composite interval mapping (CIM) analysis revealed a strong QTL associated with TARSC resistance. The QTL was confirmed in multiple genetic backgrounds. Genetic map loci are represented in cM, with position zero being the first (most distal) marker known at the beginning of the chromosome on Monsanto's internal consensus genetic map. The QTL peaks from these bi-parental mapping populations were located on chromosome 10 within 8.3 cM to 11.9 cM on Monsanto's internal consensus genetic map. Combining the CIM data from these mapping populations, the interval for this QTL was 0-17.8 cM (0-74.5 IcM). The additive effect for one copy of a favorable allele was a reduction of 0.9-2.44 TARSC rating score. The phenotypic variance explained ($R^2$) by this QTL was 43-75% (Table 6).

TABLE 6

CIM results from each mapping population.

| Mapping population | #Mk | Resistant Parent | Chr | QTL peak | Left | Right | p-value | Additive | QTL $R^2$ | Total $R^2$ |
|---|---|---|---|---|---|---|---|---|---|---|
| A | 154 | CV001735 | 10 | 11.9 | 7.2 | 16.7 | 0.01 | 2.44 | 0.71 | 0.78 |
| B | 170 | CV001735 | 10 | 8.3 | 6.1 | 16.7 | 0.01 | 1.73 | 0.57 | 0.75 |

TABLE 6-continued

CIM results from each mapping population.

| Mapping population | #Mk | Resistant Parent | Chr | QTL peak | Left | Right | p-value | Additive | QTL $R^2$ | Total $R^2$ |
|---|---|---|---|---|---|---|---|---|---|---|
| C | 155 | CV001735 | 10 | 10.9 | 4.5 | 16.7 | 0.01 | 2.15 | 0.75 | 0.86 |
| D | 152 | CV001735 | 10 | 7.2 | 0 | 17.8 | 0.01 | 0.9 | 0.43 | 0.6 |

*p-value is based on 1,000 permutation tests

Each row of Table 6 provides mapping population ID, number of SNP markers genotyped, resistant parent, chromosome position, the peak of the Likelihood ratio corresponds to TARSC resistance, QTL interval where left and right flanking positions are shown, p-value, additive effect, and the phenotypic variance ($R^2$) of individual QTL or Total QTLs.

Table 7 lists the effect estimates on TARSC rating score for each marker (SEQ ID NO) linked to TARSC resistance based on SMA. Each row provides the SEQ ID NO of the marker, marker position on Monsanto's internal consensus genetic map and the Neighbors 2008 maize genomic map (publicly available at Maize GDB website), cross, genetic source of favorable allele, F statistical value, favorable allele, unfavorable allele, the estimated effect that the marker polymorphism had on the TARSC rating score and p-value based on permutation test. The QTL interval was 3.99-17.7 cM on chromosome 10 of Monsanto internal consensus genetic map. This QTL was designated as "TARSC-10.01".

For example, SEQ ID NO: 1 was associated with a 1.3-1.9 reduction in TARSC rating score by one copy of the favorable allele depending on mapping populations.

Example 2. Fine-Mapping of TARSC-10.01 by Joint Linkage Mapping (JLM)

As shown in Example 1, TARSC-10.01 was identified from four bi-parental mapping populations by crossing one resistant line with four different susceptible lines. Three of these mapping populations (A, B, and C) were merged for joint linkage mapping using the least absolute shrinkage and selection operator (LASSO) model. 95% best markers based on bootstrapping probability were identified within 9.4-13.7 cM on chromosome 10 of Monsanto's internal consensus genetic map (Table 8). The QTL peak associated with TARSC-10.01 was mapped to 12.2 cM. The additive effect for one copy of favorable allele was a reduction of 2.01 TARSC rating score. The phenotypic variance explained ($R^2$) by this QTL was 67%.

TABLE 7

Estimate effects of markers linked to TARSC-10.01 by SMA.

| SEQ ID NO. | MON Map cM | IBM2008 Map IcM | Cross | Genetic Source of Favorable Allele | Fstat | Favorable allele | Unfavorable allele | Single Allele Effect | Permutation testing Probability |
|---|---|---|---|---|---|---|---|---|---|
| 1 | 3.99 | 8 | CV001735/CV001988*2 | CV001735 | 120.3 | C | T | 1.7 | 0.001 |
| 1 | 3.99 | 8 | CV004755*2/CV001735 | CV001735 | 243.2 | C | T | 1.9 | 0.001 |
| 1 | 3.99 | 8 | CV004552*2/CV001735 | CV001735 | 114.3 | C | T | 1.3 | 0.001 |
| 2 | 7.27 | 29.9 | CV001735/CV001988*2 | CV001735 | 152.4 | T | C | 1.8 | 0.001 |
| 2 | 7.27 | 29.9 | CV004755*2/CV001735 | CV001735 | 347.2 | T | C | 2 | 0.001 |
| 2 | 7.27 | 29.9 | CV004552*2/CV001735 | CV001735 | 198.4 | T | C | 1.6 | 0.001 |
| 3 | 8.9 | 33.8 | CV001735/CV001988*2 | CV001735 | 314.1 | T | C | 2.1 | 0.001 |
| 3 | 8.9 | 33.8 | CV004755*2/CV001735 | CV001735 | 492.5 | T | C | 2.1 | 0.001 |
| 4 | 9.39 | 35.8 | CV004552*2/CV001735 | CV001735 | 255.6 | C | T | 1.7 | 0.001 |
| 5 | 12.2 | 50.3 | CV001735/CV001988*2 | CV001735 | 484.3 | G | A | 2.3 | 0.001 |
| 5 | 12.2 | 50.3 | CV004755*2/CV001735 | CV001735 | 601.7 | G | A | 2.1 | 0.001 |
| 6 | 13.69 | 57.5 | CV001735/CV001988*2 | CV001735 | 292.8 | T | G | 2.1 | 0.001 |
| 6 | 13.69 | 57.5 | CV004755*2/CV001735 | CV001735 | 348.5 | T | G | 2 | 0.001 |
| 6 | 13.69 | 57.5 | CV004552*2/CV001735 | CV001735 | 181.9 | T | G | 1.5 | 0.001 |
| 7 | 17.7 | 74.1 | CV001735/CV001988*2 | CV001735 | 209.2 | G | A | 2 | 0.001 |
| 7 | 17.7 | 74.1 | CV004755*2/CV001735 | CV001735 | 242.4 | G | A | 1.9 | 0.001 |
| 7 | 17.7 | 74.1 | CV004552*2/CV001735 | CV001735 | 117.9 | G | A | 1.3 | 0.001 |

*p-value is based on 10,000 permutation tests

TABLE 8

Fine-mapping of TARSC-10.01 by JLM.

| #Mk | Chr | QTL peak | Left | Right | p-value | Additive | QTL $R^2$ | Total $R^2$ |
|---|---|---|---|---|---|---|---|---|
| 296 | 10 | 12.2 | 9.4 | 13.7 | 0.01 | 2.01 | 0.67 | 0.71 |

Table 8 provides number of markers genotyped, chromosome position, QTL peak position, QTL interval where left and right flanking positions are shown, p-value, additive effect, and phenotypic variance ($R^2$) of individual QTL or Total QTLs.

Example 3. Initial Validation of TARSC-10.01

CV001735 had a TARSC rating score of 1 and carries the favorable alleles at the TARSC-10.01 marker loci SEQ ID NO: 3 and SEQ ID NO: 5. CV004755 had a TARSC score of 8 and carries the unfavorable alleles at TARSC-10.01 marker loci SEQ ID NO: 3 and SEQ ID NO: 5. Doubled-haploid plants derived from CV004755*2/CV001735 were developed to evaluate TARSC-10.01. Doubled-haploid plants were measured for TARSC resistance and genotyped using the methods described in Example 1. Doubled-haploid plants carrying the favorable alleles at TARSC-10.01 showed a reduction of 4.2 TARSC rating score (6.1-1.9=4.2) when compared to doubled-haploid plants carrying the unfavorable alleles (Table 9). The "favorable" and "unfavorable" alleles in this case are directed to the resistant parental line CV001735 and the susceptible parental line CV004755. However, one of skill in the art will recognize that "favorable" allele at one locus may be an "unfavorable" allele in a different genetic background. Thus, the invention is not limited to the "favorable" and "unfavorable" alleles exemplified herein.

TABLE 9

Validation of TARSC-10.01

|  | DH with favorable alleles | DH with unfavorable alleles |
|---|---|---|
| Mean TARSC score | 1.928571429 | 6.166666667 |
| Standard deviation | 0.534522484 | 1.705383632 |
| *p-value | 8.87363E-07 | |

*Student t-test was used to calculate p-value.

One hundred sixteen F3 or F4 inbred plants were derived from five bi-parental populations: CV001735/CV774864, CV514093/CV001735, CV679619/CV001735, CV533507/CV001735 and CV169819/CV001735. These inbred plants were crossed with one highly susceptible tester to generate the hybrid plants for efficacy and yield protection tests of TARSC-10.01 under natural disease pressure. Four SNP markers within TARSC-10.01 interval: SEQ ID NO: 4, SEQ ID NO: 5, SEQ ID NO: 36, and SEQ ID NO: 6, were used in genotyping. The marker having SEQ ID NO: 36 was developed to increase the marker density (Table 10).

TABLE 10

Primers and probes for detecting SEQ ID NO: 36.

| | | SEQ ID NO. | | | |
|---|---|---|---|---|---|
| SEQ ID NO. | SNP Position | Fwd Primer | Rev Primer | Probe 1 | Probe 2 |
| 36 | 61 | 37 | 38 | 39 | 40 |

CV001735 carries the favorable alleles at the TARSC-10.01 marker loci: SEQ ID NO: 4, SEQ ID NO: 5, SEQ ID NO: 36, and SEQ ID NO: 6. Hybrid plants carrying the favorable alleles at these loci showed a reduction of 5.96 in TARSC rating score (8.18-2.22=5.96) and a yield advantage of 25 quintal per hectare (61.7-36.7=25) when compared to hybrid plants carrying the unfavorable alleles. "Recombined" in Table 11 refers to the existence of both favorable and unfavorable alleles within the TARSC-10.01 interval due to chromosome recombination. Hybrid plants carrying recombined alleles showed an intermediate level of TARSC resistance and yield (Table 11). The correlation analysis predicted an increased yield of 4.2 quintal per hectare for a decrease of 1 TARSC rating score (Prediction model: Yield=73.1-4.2×TARSC).

TABLE 11

Efficacy and yield protection tests of TARSC-10.01.

| TARSC-10.01 | Mean (TARSC) | Standard Error | Efficacy | p-value |
|---|---|---|---|---|
| unfavorable alleles | 8.18 | 0.31 | 5.96 | 8.77E-24 |
| favorable alleles | 2.22 | 0.37 | | |
| recombined | 4.62 | 0.47 | | |

| TARSC-10.01 | Mean (Yield) | Standard Error | Yield Protection | p-value |
|---|---|---|---|---|
| unfavorable alleles | 36.7 | 2.3 | 25 | 7.62E-12 |
| favorable alleles | 61.7 | 2.7 | | |
| recombined | 51.2 | 3.4 | | |

The estimated effects of SEQ ID NO: 4, SEQ ID NO: 5, and SEQ ID NO: 6 on TARSC rating score are shown in Table 7. SEQ ID NO: 36 was associated with a reduction of 2.98 TARSC rating score by one copy of the favorable allele based on hybrid mapping populations (Table 12).

TABLE 12

Estimate effect of SEQ ID NO: 36 by SMA.

| SEQ ID NO. | MON Map cM | IBM2008 Map IcM | Cross | Genetic Source of Favorable Allele | Fstat | Favorable allele | Unfavorable allele | Single Allele Effect | Permutation testing Probability |
|---|---|---|---|---|---|---|---|---|---|
| 36 | 12.89 | 52.8 | Hybrid | CV001735 | 6.265841 | A | C | 2.98 | 1.05E-08 |

Example 4. Further Validation of TARSC-10.01

Doubled-haploid plants were derived from CV001735/CV001988*2 BC1, CV001735/CV004755*2 BC1, and CV001735/CV004552*2 BC1. These doubled-haploid plants were then crossed with testers CV072092 or CV072867 to develop hybrid plants for further efficacy and equivalency trials of TARSC-10.01 (Table 13). Hybrid plants were measured for TARSC resistance and genotyped using the methods described in Example 1.

TABLE 13

| Population for further validation | | |
| --- | --- | --- |
| Donor Parent | Recurrent Parent | Tester |
| CV001735 | CV001988 | CV072092 |
| | CV004755 | |
| | CV004552 | |
| | CV001988 | CV072867 |
| | CV004755 | |
| | CV004552 | |

Plants were grown under natural disease infection. Each population was measured for TARSC resistance and yield. A standard statistical model was run to measure the basic statistics and to compute the heritability ($H^2$) for TARSC phenotype (Table 14). The heritability ($H^2$) was 0.82.

TABLE 14

| Basic statistics and heritability for validation populations. | |
| --- | --- |
| Mean TARSC score | 4.21 |
| Number of Lines | 1050 |
| Standard Deviation | 2.89 |
| Variance | 8.36 |
| Coefficient of Variation | 68.73 |

TABLE 14-continued

| Basic statistics and heritability for validation populations. | |
| --- | --- |
| Genetic variance | 3.05 |
| Residue variance | 0.66 |
| Total phenotypic variance | 3.71 |
| $H^2$ | 0.82 |

Hybrid plants carrying the favorable allele of TARSC-10.01 showed a reduction of 4.8 in TARSC rating score (6.2-1.4=4.8) and a yield advantage of 9.6 quintal per hectare (62.5-52.9=9.6) when compared to hybrid plants carrying the unfavorable allele (Table 15).

TABLE 15

| Further efficacy and equivalency trials of TARSC-10.01 | | | | |
| --- | --- | --- | --- | --- |
| TARSC-10.01 | Mean (TARSC) | SE | Efficacy | p-value |
| recurrent parent | 6.791666667 | 0.299345 | | |
| unfavorable alleles | 6.215568862 | 0.11348 | 4.8 | 8.8E−127 |
| favorable alleles | 1.427272727 | 0.114166 | | |
| donor parent | 1.00 | 0.14 | | |
| TARSC-10.01 | Mean (Yield) | SE | Equivalency | p-value |
| recurrent parent | 63.78879676 | 2.430292 | | |
| unfavorable alleles | 52.91514803 | 2.11918 | 9.6 | 0.000565 |
| favorable alleles | 62.50581608 | 2.169839 | | |
| donor parent | 68.05 | 7.89 | | |

Example 5. Candidate Genes within TARSC-10.01

Table 16 lists annotated coding sequences within TARSC-10.01 region. Each row provides gene ID, gene annotation, chromosome location, genetic position on Monsanto internal consensus map and physical position based on Arizona Genomics Institute B73 RefGen v2 sequence, which is publicly available. Transgenic maize resistant to tar spot complex disease can be created using these annotated genes as described in the specification.

TABLE 16

| Candidate genes within TARSC-10.01 interval. | | | | | |
| --- | --- | --- | --- | --- | --- |
| Gene | | | MON Map | Physical Map Position bp †† | |
| ID | Annotation | | Chr | cM † | Start | End |
| 1 | GRAS family transcription factor containing protein n = 1 Tax = *Oryza sativa Japonica* Group RepID = Q2QXZ6_ORYSJ (1e−179); GRAS: GRAS family transcription factor (7.1e−115); GO_MF:GO:0016874, ligase activity# (7e−35); GO_BP:GO:0045449, regulation of transcription# (1e−179); GO_CC:GO:0005634, nucleus# (6e−86) | 10 | 4.5 | 1887327 | 1889588 |
| 2 | H0716A07.11 protein n = 1 Tax = *Oryza sativa* RepID = Q01MA7_ORYSA (1e−175); Peptidase_S8: Subtilase family (4.7e−07); PA: PA domain (9.8e−05); GO_MF:GO:0043086, negative regulation of catalytic activity# (0.0); GO_BP:GO:0043086, negative regulation of catalytic activity# (0.0); GO_CC:GO:0009505, IDA#expansin# (1e−104) | 10 | 4.5 | 1891328 | 1894422 |
| 3 | Pentatricopeptide repeat-containing protein, putative n = 1 Tax = *Ricinus communis* RepID = B9RGG4_RICCO (3e−09); GO_BP:GO:0008380, RNA splicing# (6e−13) | 10 | 4.6 | 1902246 | 1905367 |

TABLE 16-continued

Candidate genes within TARSC-10.01 interval.

| Gene ID | Annotation | Chr | MON Map cM † | Physical Map Position bp †† Start | End |
|---|---|---|---|---|---|
| 4 | Protein kinase n = 1 Tax = *Zea mays* RepID = B6SVB5_MAIZE (1e−171); Lectin_legB: Legume lectin domain (5.7e−60); SKG6: Transmembrane alpha-helix domain (0.052); Pkinase: Protein kinase domain (9.1e−37); Pkinase_Tyr: Protein tyrosine kinase (1.3e−20); APH: Phosphotransferase enzyme family (0.002); GO_MF:GO:0005529, sugar binding# (0.0); GO_BP:GO:0006468, protein amino acid phosphorylation# (0.0); GO_CC:GO:0005634, nucleus# (2e−79) | 10 | 4.6 | 1915531 | 1918072 |
| 5 | Putative uncharacterized protein Sb08g001210 n = 1 Tax = *Sorghum bicolor* RepID = C5YQJ8_SORBI (2e−11) | 10 | 4.6 | 1910556 | 1911044 |
| 6 | H0701F11.1 protein n = 2 Tax = *Oryza sativa* RepID = Q259L5_ORYSA (4e−23) | 10 | 4.7 | 1938061 | 1938414 |
| 7 | OSIGBa0132I10.2 protein n = 2 Tax = *Oryza sativa* RepID = Q01MZ9_ORYSA (2e−77); Dimerisation: Dimerisation domain (4.9e−10); Methyltransf_2: O-methyltransferase (2.3e−65); Methyltransf_11: Methyltransferase domain (0.0059); Methyltransf_12: Methyltransferase domain (0.011); GO_MF:GO:0046983, protein dimerization activity# (8e−92) | 10 | 4.7 | 1933831 | 1935273 |
| 8 | OSIGBa0132I10.2 protein n = 2 Tax = *Oryza sativa* RepID = Q01MZ9_ORYSA (4e−76); Dimerisation: Dimerisation domain (4.9e−10); Methyltransf_2: O-methyltransferase (5.5e−68); Methyltransf_11: Methyltransferase domain (0.0093); Methyltransf_12: Methyltransferase domain (0.0011); GO_MF:GO:0046983, protein dimerization activity# (4e−91) | 10 | 4.7 | 1919383 | 1920925 |
| 9 | Probable calcium-transporting ATPase 4, plasma membrane-type n = 5 Tax = *Oryza sativa* RepID = ACA4_ORYSJ (0.0); Cation_ATPase_N: Cation transporter/ATPase, N-terminus (9.9e−13); E1-E2_ATPase: E1-E2 ATPase (7.6e−76); Hydrolase: haloacid dehalogenase-like hydrolase (1.1e−16); Cation_ATPase_C: Cation transporting ATPase, C-terminus (3.1e−57); GO_MF:GO:0046872, metal ion binding# (0.0); GO_BP:GO:0016820, hydrolase activity, acting on acid anhydrides, catalyzing transmembrane movement of substances# (0.0); GO_CC:GO:0016021, integral to membrane# (0.0) | 10 | 4.7 | 1925238 | 1929716 |
| 10 | Cytosolic ADP-glucose pyrophosphorylase small subunit n = 7 Tax = Poaceae RepID = D3YKV1_MAIZE (5e−98); NTP_transferase: Nucleolidyl transferase (2.1e−27); GO_MF:GO:0016779, nucleotidyltransferase activity# (1e−97); GO_BP:GO:0009058, biosynthetic process# (1e−97); GO_CC:GO:0009507, chloroplast# (1e−97) | 10 | 4.8 | 1941294 | 1942169 |
| 11 | Heterogeneous nuclear ribonucleoprotein R n = 1 Tax = *Zea mays* RepID = B6U752_MAIZE (1e−174); RRM_1: RNA recognition motif, (a.k.a. RRM, RB (2.2e−19); RRM_1: RNA recognition motif, (a.k.a. RRM, RB (3.7e−06); RRM_1: RNA recognition motif, (a.k.a. RRM, RB (1.9e−14); GO_MF:GO:0003676, nucleic acid binding# (1e−174); GO_BP:GO:0006355, regulation of transcription, DNA-dependent# (1e−133); GO_CC:GO:0030529, ribonucleoprotein complex# (1e−174) | 10 | 4.8 | 1947546 | 1956901 |
| 12 | Mitochondrial glycoprotein n = 1 Tax = *Zea mays* RepID = B6TZZ4_MAIZE (9e−59); GO_CC:GO:0005759, IEP#mitochondrial matrix# (9e−59) | 10 | 4.8 | 1945817 | 1947527 |
| 13 | Transposon protein n = 3 Tax = Andropogoneae RepID = B6SWU7_MAIZE (7e−31); GO_MF:GO:0046983, protein dimerization activity# (6e−31) | 10 | 4.8 | 1938905 | 1939745 |
| 14 | Xylanase inhibitor protein 1 n = 1 Tax = *Zea mays* RepID = B6U3V2_MAIZE (1e−154); Glyco_hydro_18: Glycosyl hydrolases family 18 (2e−21); GO_MF:GO:0043169, cation binding# (1e−154); GO_BP:GO:0045493, xylan catabolic process# (1e−154); GO_CC:GO:0005576, extracellular region# (2e−75) | 10 | 5 | 1981032 | 1982105 |
| 15 | Retrotransposon protein, putative, unclassified n = 1 Tax = *Oryza sativa Japonica* Group RepID = Q2QNF1_ORYSJ (3e−28); GO_MF:GO:0003964, RNA-directed DNA polymerase, group II intron encoded# (2e−32); GO_BP:GO:0006278, RNA-dependent DNA replication# (2e−32) | 10 | 5.1 | 2016346 | 2016912 |
| 16 | Triose phosphate/phosphate translocator, non-green plastid, chloroplast, putative n = 1 Tax = *Ricinus communis* RepID = B9RP61_RICCO (8e−85); TPT: Triose-phosphate Transporter family (1.9e−48); GO_MF:GO:0046983, protein dimerization activity# (4e−96); GO_BP:GO:0006355, regulation of transcription, DNA-dependent# (4e−96); GO_CC:GO:0016021, integral to membrane# (4e−96) | 10 | 5.1 | 2005944 | 2007695 |

TABLE 16-continued

Candidate genes within TARSC-10.01 interval.

| Gene ID | Annotation | Chr | MON Map cM † | Physical Map Position bp †† Start | End |
|---|---|---|---|---|---|
| 17 | Probable protein NAP1 n = 4 Tax = *Oryza sativa* RepID = NCKP1_ORYSJ (0.0); Nckap1: Membrane-associated apoptosis protein (2.6e-08); GO_MF:GO:0016563, transcription activator activity# (0.0); GO_BP:GO:0045010, PMID: 11559594#actin nucleation# (0.0); GO_CC:GO:0031209, TAS#SCAR complex# (0.0) | 10 | 5.15 | 2009109 | 2031170 |
| 18 | Glucosamine--fructose-6-phosphate aminotransferase n = 1 Tax = *Chlamydomonas reinhardtii* RepID = A8IZE7_CHLRE (2e-14); GO_MF:GO:0005529, sugar binding# (8e-24); GO_BP:GO:0005975, carbohydrate metabolic process# (8e-24); GO_CC:GO:0005737, cytoplasm# (9e-24) | 10 | 5.2 | 2036993 | 2037474 |
| 19 | PPR-817 n = 5 Tax = *Zea mays* RepID = C9W4B9_MAIZE (2e-52); PPR: PPR repeat (0.11); PPR: PPR repeat (9e-06); PPR: PPR repeat (0.00088); GO_MF:GO:0003723, RNA binding# (8e-19); GO_BP:GO:0008152, metabolic process# (6e-16); GO_CC:GO:0005739, mitochondrion# (6e-19) | 10 | 5.2 | 2038169 | 2040783 |
| 20 | Nitrous oxide reductase, N-terminal n = 1 Tax = *Medicago truncatula* RepID = Q2HUV7_MEDTR (6e-82); WD40: WD domain, G-beta repeat (0.0081); WD40: WD domain, G-beta repeat (6.3); WD40: WD domain, G-beta repeat (0.41); GO_MF:GO:0008270, zinc ion binding# (6e-24); GO_BP:GO:0046822, regulation of nucleocytoplasmic transport# (1e-23); GO_CC:GO:0005643, nuclear pore# (1e-23) | 10 | 5.3 | 2043905 | 2048914 |
| 21 | Putative RGH1A n = 2 Tax = *Oryza sativa Japonica* Group RepID = Q6YYL2_ORYSJ (1e-144); NB-ARC: NB-ARC domain (3.2e-44); LRR_1: Leucine Rich Repeat (2.7e+02); LRR_1: Leucine Rich Repeat (95); LRR_1: Leucine Rich Repeat (3.6); LRR_1: Leucine Rich Repeat (9.8); LRR_1: Leucine Rich Repeat (2.1e+02); GO_MF:GO:0005524, ATP binding# (0.0); GO_BP:GO:0006952, defense response# (0.0) | 10 | 5.3 | 2049440 | 2056061 |
| 22 | Tyrosine-specific protein phosphatase-like n = 3 Tax = *Oryza sativa* RepID = Q6K4X2_ORYSJ (1e-168); Peptidase_C12: Ubiquitin carboxyl-terminal hydrolase, family 1 (1.8e-37); GO_MF:GO:0005529, sugar binding# (1e-138); GO_BP:GO:0048544, recognition of pollen# (1e-138); GO_CC:GO:0005622, intracellular# (1e-57) | 10 | 5.3 | 2041587 | 2042966 |
| 23 | Nitrous oxide reductase, N-terminal n = 1 Tax = *Medicago truncatula* RepID = Q2HUV7_MEDTR (4e-81); GO_MF:GO:0003674, ND#molecular_function# (2e-13); GO_BP:GO:0046822, regulation of nucleocytoplasmic transport# (2e-13); GO_CC:GO:0005643, nuclear pore# (2e-13) | 10 | 5.6 | 2113564 | 2115738 |
| 24 | Putative RGH1A n = 2 Tax = *Oryza sativa Japonica* Group RepID = Q6YYL2_ORYSJ (1e-130); NB-ARC: NB-ARC domain (4.9e-51); NACHT: NACHT domain (0.081); LRR_1: Leucine Rich Repeat (95); LRR_1: Leucine Rich Repeat (7.3); LRR_1: Leucine Rich Repeat (22); GO_MF:GO:0005524, ATP binding# (0.0); GO_BP:GO:0006952, defense response# (0.0) | 10 | 5.65 | 2124313 | 2130577 |
| 25 | VQ n = 2 Tax = *Zea mays* RepID = B6UIL9_MAIZE (7e-33); VQ: VQ motif (8.9e-08) | 10 | 5.7 | 2141505 | 2142516 |
| 26 | FAD dependent oxidoreductase superfamily n = 1 Tax = *Talaromyces stipitatus* ATCC 10500 RepID = B8MNY1_TALSN (3e-17); SMC_Nse1: Nse1 non-SMC component of SMC5-6 complex (3.3e-49); zf-C3HC4: Zinc finger, C3HC4 type (RING finger) (0.059); zf-RING-like: RING-like domain (2.7e-11); GO_MF:GO:0008270, zinc ion binding# (3e-83); GO_BP:GO:0006974, response to DNA damage stimulus# (1e-15); GO_CC:GO:0005634, nucleus# (1e-15) | 10 | 6.1 | 2229071 | 2233001 |
| 27 | NHL25 n = 1 Tax = *Zea mays* RepID = B6SML6_MAIZE (2e-30); Hin1: Harpin-induced protein 1 (Hin1) (3.8e-31) | 10 | 6.1 | 2227313 | 2228642 |
| 28 | Putative uncharacterized protein n = 1 Tax = *Zea mays* RepID = B4FB22_MAIZE (1e-161); GO_MF:GO:0003677, DNA binding# (2e-15); GO_BP:GO:0045449, regulation of transcription# (2e-15); GO_CC:GO:0005634, nucleus# (2e-15) | 10 | 6.1 | 2223053 | 2227012 |
| 29 | 117M18_7 n = 1 Tax = *Brassica rapa* RepID = Q4AC18_BRACM (9e-61); DUF618: Protein of unknown function, DUF618 (2e-23); GO_MF:GO:0003964, RNA-directed DNA polymerase, group II intron encoded# (4e-60); GO_BP:GO:0006278, RNA-dependent DNA replication# (4e-60) | 10 | 6.25 | 2249241 | 2256304 |
| 30 | NB-ARC domain containing protein n = 3 Tax = *Oryza sativa* RepID = Q10KL3_ORYSJ (0.0); NB-ARC: NB-ARC domain (4.1e-16); NACHT: NACHT domain (0.081); LRR_1: Leucine Rich Repeat (2.6e+02); LRR_1: Leucine Rich Repeat (3.9); LRR_1: Leucine Rich Repeat (9); LRR_1: Leucine Rich Repeat | 10 | 6.3 | 2257206 | 2260980 |

TABLE 16-continued

Candidate genes within TARSC-10.01 interval.

| Gene ID | Annotation | Chr | MON Map cM † | Physical Map Position bp †† Start | End |
|---|---|---|---|---|---|
| | (1.2e+02); GO_MF:GO:0005524, ATP binding# (0.0); GO_BP:GO:0006952, defense response# (0.0) | | | | |
| 31 | Homoserine dehydrogenase n = 3 Tax = Andropogoneae RepID = C5YQR0_SORBI (1e-123); NAD_binding_3: Homoserine dehydrogenase, NAD binding domain (0.023); Homoserine_dh: Homoserine dehydrogenase (5.8e-09); GO_MF:GO:0050661, NADP or NADPH binding# (1e-112); GO_BP:GO:0055114, oxidation reduction# (1e-112); GO_CC:GO:0009536, plastid# (2e-28) | 10 | 7.15 | 2446343 | 2450352 |
| 32 | Bubr1, putative n = 1 Tax = *Ricinus communis* RepID = B9R8U9_RICCO (2e-20); Mad3_BUB1_I: Mad3/BUB1 homology region 1 (4e-43); GO_MF:GO:0005524, ATP binding# (2e-19); GO_BP:GO:0007094, IDA#mitotic cell cycle spindle assembly checkpoint# (5e-21); GO_CC:GO:0010369, IDA#chromocenter# (5e-21) | 10 | 7.2 | 2451389 | 2453298 |
| 33 | Putative uncharacterized protein Sb08g001730 n = 1 Tax = *Sorghum bicolor* RepID = C5YQR1_SORBI (1e-132) | 10 | 7.2 | 2453306 | 2454902 |
| 34 | Putative uncharacterized protein Sb08g001750 n = 1 Tax = *Sorghum bicolor* RepID = C5YQR3_SORBI (2e-14) | 10 | 7.2 | 2455677 | 2456555 |
| 35 | UDP-N-acetylglucosamine transferase subunit ALG14, related n = 1 Tax = *Medicago truncatula* RepID = Q2HUA0_MEDTR (5e-70); Alg14: Oligosaccharide biosynthesis protein A (1.5e-91); GO_MF:GO:0016740, transferase activity# (5e-70); GO_BP:GO:0016301, kinase activity# (3e-29); GO_CC:GO:0016021, integral to membrane# (4e-36) | 10 | 7.2 | 2457981 | 2463565 |
| 36 | R2r3-myb transcription factor, putative n = 1 Tax = *Ricinus communis* RepID = B9SY81_RICCO (3e-66); Myb_DNA-binding: Myb-like DNA-binding domain (2.3e-10); Myb_DNA-binding: Myb-like DNA-binding domain (1.3e-09); GO_MF:GO:0003677, DNA binding# (3e-69); GO_BP:GO:0045449, regulation of transcription# (3e-69); GO_CC:GO:0005634, nucleus# (3e-69) | 10 | 7.25 | 2466106 | 2468014 |
| 37 | CDC45 (Cell division cycle 45)-like protein (ISS) n = 1 Tax = *Ostreococcus tauri* RepID = Q01AB6_OSTTA (9e-63); CDC45: CDC45-like protein (2.8e-117); GO_MF:GO:0005515, protein binding# (1e-48); GO_BP:GO:0006270, DNA replication initiation# (0.0); GO_CC:GO:0005634, nucleus# (5e-53) | 10 | 7.3 | 2479535 | 2481912 |
| 38 | MYB60-like protein n = 1 Tax = *Citrus macrophylla* RepID = A0T1L7_9ROSI (1e-46); Myb_DNA-binding: Myb-like DNA-binding domain (1.8e-06); Myb_DNA-binding: Myb-like DNA-binding domain (6.9e-09); GO_MF:GO:0003677, DNA binding# (3e-47); GO_BP:GO:0045449, regulation of transcription# (3e-47); GO_CC:GO:0005634, nucleus# (3e-47) | 10 | 8 | 2633117 | 2634016 |
| 39 | R2R3 Myb30 transcription factor n = 2 Tax = *Vitis vinifera* RepID = A0T1L8_VITVI (3e-52); Myb_DNA-binding: Myb-like DNA-binding domain (2.8e-06); Myb_DNA-binding: Myb-like DNA-binding domain (1.3e-09); GO_MF:GO:0003677, DNA binding# (3e-52); GO_BP:GO:0045449, regulation of transcription# (3e-52); GO_CC:GO:0005634, nucleus# (3e-52) | 10 | 8 | 2626992 | 2627929 |
| 40 | ZF-HD protein dimerisation region containing protein n = 5 Tax = *Oryza sativa* RepID = Q2QYC5_ORYSJ (7e-18); ZF-HD_dimer: ZF-HD protein dimerisation region (5.7e-35); GO_MF:GO:0003677, DNA binding# (2e-16); GO_BP:GO:0045449, regulation of transcription# (1e-10) | 10 | 8 | 2630370 | 2630666 |
| 41 | Zinc finger homeodomain protein 1 n = 2 Tax = *Zea mays* RepID = B6TUP8_MAIZE (1e-17); ZF-HD_dimer: ZF-HD protein dimerisation region (2e-35); GO_MF:GO:0003677, DNA binding# (1e-17); GO_BP:GO:0045449, regulation of transcription# (1e-10) | 10 | 8 | 2636712 | 2637008 |
| 42 | 40S ribosomal protein S16 n = 4 Tax = Andropogoneae RepID = B6TVN0_MAIZE (2e-79); Ribosomal_S9: Ribosomal protein S9/S16 (1.9e-74); GO_MF:GO:0003735, structural constituent of ribosome# (2e-79); GO_BP:GO:0006412, translation# (2e-79); GO_CC:GO:0030529, ribonucleoprotein complex# (2e-79) | 10 | 8.1 | 2656675 | 2657124 |
| 43 | GAST1 protein n = 1 Tax = *Zea mays* RepID = B6TAW1_MAIZE (3e-36); GRP: Glycine rich protein family (0.0083); GASA: Gibberellin regulated protein (8.5e-40); GO_MF:GO:0005515, protein binding# (1e-20); GO_BP:GO:0009750, IEP#response to fructose stimulus# (2e-24); GO_CC:GO:0005576, extracellular region# (7e-22) | 10 | 8.1 | 2647007 | 2648234 |

TABLE 16-continued

Candidate genes within TARSC-10.01 interval.

| Gene ID | Annotation | Chr | MON Map cM † | Physical Map Position bp †† Start | End |
|---|---|---|---|---|---|
| 44 | Secondary cell wall-related glycosyltransferase family 47 n = 1 Tax = *Zea mays* RepID = B6U626_MAIZE (0.0); Exostosin: Exostosin family (2.8e−107); GO_MF:GO:0016740, transferase activity# (0.0); GO_BP:GO:0048868, IMP#pollen tube development# (1e−133); GO_CC:GO:0016020, membrane# (0.0) | 10 | 8.1 | 2650266 | 2653597 |
| 45 | Trigger factor, putative n = 1 Tax = *Ricinus communis* RepID = B9SYY0_RICCO (1e−157); Trigger_N: Bacterial trigger factor protein (TF) (2.2e−22); FKBP_C: FKBP-type peptidyl-prolyl cis-trans isomeras (0.0049); Trigger_C: Bacterial trigger factor protein (TF) C-terminus (6.8e−25); GO_MF:GO:0003755, parvulin# (0.0); GO_BP:GO:0015031, protein transport# (0.0); GO_CC:GO:0009941, IDA#chloroplast envelope# (1e−150) | 10 | 8.15 | 2657714 | 2664935 |
| 46 | NAC domain protein NAC5 n = 1 Tax = *Gossypium hirsutum* RepID = C0J1R6_GOSHI (5e−64); NAM: No apical meristem (NAM) protein (1.5e−80); GO_MF:GO:0003677, DNA binding# (0.0); GO_BP:GO:0045449, regulation of transcription# (0.0); GO_CC:GO:0005634, nucleus# (2e−57) | 10 | 8.2 | 2679214 | 2681450 |
| 47 | Ferredoxin n = 2 Tax = Andropogoneae RepID = Q9SLP6_MAIZE (2e−51); NAD_binding_1: Oxidoreductase NAD-binding domain (4.3e−17); GO_MF:GO:0050661, NADP or NADPH binding# (2e−51); GO_BP:GO:0055114, oxidation reduction# (2e−51); GO_CC:GO:0042651, thylakoid membrane# (2e−51) | 10 | 8.3 | 2691991 | 2694227 |
| 48 | Putative uncharacterized protein Sb04g002490 n = 2 Tax = Andropogoneae RepID = C5XTT2_SORBI (3e−41); GO_CC:GO:0009941, IDA#chloroplast envelope# (2e−24) | 10 | 8.3 | 2688438 | 2689340 |
| 49 | GDA1/CD39 family protein n = 3 Tax = *Oryza sativa* RepID = Q2RB41_ORYSJ (1e−158); GDA1_CD39: GDA1/CD39 (nucleoside phosphatase) family (3e−127); GO_MF:GO:0016787, hydrolase activity# (1e−161); GO_BP:GO:0009846, IGI#pollen germination# (1e−101); GO_CC:GO:0016021, integral to membrane# (1e−103) | 10 | 8.6 | 2760826 | 2763168 |
| 50 | Putative uncharacterized protein n = 1 Tax = *Zea mays* RepID = B7ZZA0_MAIZE (9e−27) | 10 | 8.7 | 2779686 | 2780300 |
| 51 | EMB2748 n = 2 Tax = *Zea mays* RepID = B6SKC7_MAIZE (1e−152); GO_CC:GO:0009536, plastid# (3e−27) | 10 | 8.8 | 2788657 | 2793051 |
| 52 | NB-ARC domain containing protein n = 2 Tax = *Oryza sativa* RepID = Q2R057_ORYSJ (7e−60); GO_MF:GO:0005524, ATP binding# (1e−121); GO_BP:GO:0006952, defense response# (1e−121) | 10 | 8.9 | 2842719 | 2848166 |
| 53 | Pentatricopeptide repeat-containing protein, putative n = 1 Tax = *Ricinus communis* RepID = B9RY36_RICCO (1e−136); PPR: PPR repeat (0.12); PPR: PPR repeat (2.4e−10); PPR: PPR repeat (7e−12); PPR: PPR repeat (3e−11); PPR: PPR repeat (1e−09); PPR: PPR repeat (2.2e−10); PPR: PPR repeat (4.4e−09); PPR: PPR repeat (1.8e−08); PPR: PPR repeat (2.5e−08); PPR: PPR repeat (6.8e−08); PPR: PPR repeat (9.8e−11); PPR: PPR repeat (2e−08); PPR: PPR repeat (2.6e−06); PPR: PPR repeat (5.7e−08); PPR: PPR repeat (0.022); GO_MF:GO:0005488, binding# (4e−75); GO_CC:GO:0005739, mitochondrion# (9e−73) | 10 | 8.9 | 2836993 | 2839104 |
| 54 | Putative glycosyltransferase n = 1 Tax = *Oryza sativa Japonica* Group RepID = Q75J72_ORYSJ (1e−159); Glyco_transf_8: Glycosyl transferase family 8 (3.7e−44); GO_MF:GO:0016757, transferase activity, transferring glycosyl groups# (0.0); GO_CC:GO:0005794, IDA#Golgi apparatus# (1e−135) | 10 | 8.9 | 2794574 | 2799509 |
| 55 | Putative uncharacterized protein Sb08g002010 n = 1 Tax = *Sorghum bicolor* RepID = C5YR34_SORBI (4e−17) | 10 | 8.9 | 2839300 | 2840733 |
| 56 | Atpob1, putative n = 1 Tax = *Ricinus communis* RepID = B9RCL7_RICCO (2e−11); DUF1191: Protein of unknown function (DUF1191) (2.2e−79); SKG6: Transmembrane alpha-helix domain (0.074); GO_MF:GO:0005515, protein binding# (2e−11); GO_CC:GO:0005886, plasma membrane# (2e−16) | 10 | 9.3 | 3172899 | 3173926 |
| 57 | Putative RGH1A n = 2 Tax = *Oryza sativa Japonica* Group RepID = Q6YYL2_ORYSJ (1e−151); NB-ARC: NB-ARC domain (3.4e−48); NACHT: NACHT domain (0.044); LRR_1: Leucine Rich Repeat (1.1e+02); LRR_1: Leucine Rich Repeat (1.3); LRR_1: Leucine Rich Repeat (8.1); GO_MF:GO:0005524, ATP binding# (0.0); GO_BP:GO:0006952, defense response# (0.0) | 10 | 9.3 | 2983774 | 2996704 |
| 58 | Root phototropism protein, putative n = 1 Tax = *Ricinus communis* RepID = B9TON5_RICCO (1e−120); NPH3: NPH3 family (3.2e−76); GO_MF:GO:0004871, signal transducer activity# (0.0); GO_BP:GO:0009416, IEP#response to light stimulus# (0.0); GO_CC:GO:0005886, plasma membrane# (3e−88) | 10 | 9.35 | 3184586 | 3186673 |
| 59 | Ankyrin-like protein-like protein n = 1 Tax = *Sorghum bicolor* RepID = Q84YEO_SORBI (1e−177); Ank: Ankyrin repeat (2.7); | 10 | 9.4 | 3020187 | 3025468 |

TABLE 16-continued

Candidate genes within TARSC-10.01 interval.

| Gene ID | Annotation | MON Map Chr | MON Map cM † | Physical Map Position bp †† Start | Physical Map Position bp †† End |
|---|---|---|---|---|---|
|  | Ank: Ankyrin repeat (5.1e-05); Ank: Ankyrin repeat (5.1e-05); Ank: Ankyrin repeat (0.98); Ank: Ankyrin repeat (0.15); Ank: Ankyrin repeat (0.0063); TPR_2: Tetratricopeptide repeat (22); TPR_1: Tetratricopeptide repeat (0.0035); TPR_2: Tetratricopeptide repeat (6.1e-06); GO_MF:GO:0005488, binding# (1e-177) |  |  |  |  |
| 60 | GTP binding protein, putative n = 1 Tax = *Ricinus communis* RepID = B9S1W0_RICCO (3e-26); DUF567: Protein of unknown function (DUF567) (2.4e-17) | 10 | 9.4 | 3016838 | 3018189 |
| 61 | HAT family dimerisation domain containing protein n = 3 Tax = *Oryza sativa Japonica* Group RepID = Q53RM1_ORYSJ (1e-35); hATC: hAT family dimerisation domain (6.1e-33); GO_MF:GO:0046983, protein dimerization activity# (4e-71); GO_BP:GO:0006468, protein amino acid phosphorylation# (6e-26) | 10 | 9.4 | 3026236 | 3027646 |
| 62 | Putative Xa1-like protein n = 1 Tax = *Sorghum bicolor* RepID = Q84YF1_SORBI (1e-84); GO_MF:GO:0005524, ATP binding# (1e-84); GO_BP:GO:0006952, defense response# (1e-84) | 10 | 9.4 | 3161745 | 3162817 |
| 63 | RPT2-like protein n = 1 Tax = *Zea mays* RepID = B6ST41_MAIZE (2e-76); GO_MF:GO:0005515, protein binding# (2e-76); GO_BP:GO:0009416, IEP#response to light stimulus# (2e-76); GO_CC:GO:0005886, plasma membrane# (2e-10) | 10 | 9.4 | 3190592 | 3191648 |
| 64 | RPT2-like protein n = 1 Tax = *Zea mays* RepID = B6ST41_MAIZE (2e-96); NPH3: NPH3 family (5.1e-05); GO_MF:GO:0005515, protein binding# (2e-96); GO_BP:GO:0009416, IEP#response to light stimulus# (2e-96); GO_CC:GO:0016020, membrane# (4e-24) | 10 | 9.4 | 3191803 | 3193365 |
| 65 | 50S ribosomal protein L11 n = 2 Tax = *Zea mays* RepID = B4FC48_MAIZE (1e-45); Ribosomal_L11_N: Ribosomal protein L11, N-terminal domain (2.5e-14); Ribosomal_L11: Ribosomal protein L11, RNA binding domain (2.6e-19); GO_MF:GO:0003735, structural constituent of ribosome# (1e-45); GO_BP:GO:0006412, translation# (1e-45); GO_CC:GO:0030529, ribonucleoprotein complex# (1e-45) | 10 | 9.5 | 3061376 | 3061850 |
| 66 | Obtusifoliol 14-alpha demethylase n = 3 Tax = Andropogoneae RepID = CP51_SORBI (0.0); p450: Cytochrome P450 (2e-38); GO_MF:GO:0046872, metal ion binding# (0.0); GO_BP:GO:0055114, oxidation reduction# (0.0); GO_CC:GO:0016021, integral to membrane# (0.0) | 10 | 9.5 | 3062647 | 3066766 |
| 67 | Jacalin-like lectin domain containing protein n = 1 Tax = *Oryza sativa Japonica* Group RepID = Q2R1E0_ORYSJ (7e-69); Pkinase: Protein kinase domain (4.4e-54); Pkinase_Tyr: Protein tyrosine kinase (1.6e-27); DUF260: Protein of unknown function DUF260 (8.9e-60); GO_MF:GO:0005524, ATP binding# (1e-136); GO_BP:GO:0006468, protein amino acid phosphorylation# (1e-136) | 10 | 9.7 | 3272812 | 3278667 |
| 68 | Retrotransposon protein, putative, unclassified n = 1 Tax = *Oryza sativa Japonica* Group RepID = Q7XE51_ORYSJ (1e-22); GO_MF:GO:0003964, RNA-directed DNA polymerase, group II intron encoded# (1e-22); GO_BP:GO:0006278, RNA-dependent DNA replication# (1e-22); GO_CC:GO:0000145, NAS#exocyst# (2e-10) | 10 | 9.7 | 3285297 | 3286098 |
| 69 | Chromatin remodeling complex subunit (Fragment) n = 1 Tax = *Populus trichocarpa* RepID = B9H8S6_POPTR (1e-43); GO_MF:GO:0046872, metal ion binding# (5e-57); GO_BP:GO:0016568, chromatin modification# (1e-41); GO_CC:GO:0005634, nucleus# (1e-41) | 10 | 9.8 | 3314941 | 3315935 |
| 70 | Phosphatidylinositol transporter/transporter n = 3 Tax = Andropogoneae RepID = B6U127_MAIZE (8e-22); CRAL_TRIO_N: CRAL/TRIO, N-terminus (0.00016); GO_MF:GO:0005215, transporter activity# (2e-23); GO_BP:GO:0006810, transport# (2e-23); GO_CC:GO:0005622, intracellular# (2e-23) | 10 | 9.8 | 3310795 | 3311385 |
| 71 | Tobamovirus multiplication 3 n = 2 Tax = *Zea mays* RepID = B6TCL4_MAIZE (4e-61); DUF1084: Protein of unknown function (DUF1084) (9.4e-11); GO_MF:GO:0005515, protein binding# (8e-42); GO_BP:GO:0046786, IMP#viral replication complex formation and maintenance# (8e-42); GO_CC:GO:0005886, plasma membrane# (9e-37) | 10 | 9.8 | 3311942 | 3313098 |
| 72 | Viviparous-14 n = 2 Tax = Andropogoneae RepID = B6SV18_MAIZE (1e-16); GO_MF:GO:0046872, metal ion binding# (7e-15); GO_BP:GO:0055114, oxidation reduction# (8e-11); GO_CC:GO:0009570, IDA#chloroplast stroma# (8e-11) | 10 | 9.85 | 3316030 | 3326948 |

TABLE 16-continued

Candidate genes within TARSC-10.01 interval.

| Gene ID | Annotation | Chr | MON Map cM † | Physical Map Position bp †† Start | End |
|---|---|---|---|---|---|
| 73 | Putative gag-pol polyprotein n = 1 Tax = *Zea mays* RepID = Q8SA91_MAIZE (1e−19); GO_MF:GO:0004190, penicillopepsin activity# (1e−19); GO_BP:GO:0015074, DNA integration# (1e−19); GO_CC:GO:0005634, nucleus# (1e−19) | 10 | 9.9 | 3338509 | 3340824 |
| 74 | Rust resistance protein n = 7 Tax = *Zea mays* RepID = Q6PT59_MAIZE (0.0); NB-ARC: NB-ARC domain (2.2e−47); NACHT: NACHT domain (0.011); LRR_1: Leucine Rich Repeat (13); LRR_1: Leucine Rich Repeat (5.1); LRR_1: Leucine Rich Repeat (2.9e+02); LRR_1: Leucine Rich Repeat (19); LRR_1: Leucine Rich Repeat (11); LRR_1: Leucine Rich Repeat (1.2e+02); LRR_1: Leucine Rich Repeat (2e+02); LRR_1: Leucine Rich Repeat (2.4); GO_MF:GO:0005524, ATP binding# (0.0); GO_BP:GO:0006952, defense response# (0.0) | 10 | 10 | 3368785 | 3373388 |
| 75 | P-type ATPase (Fragment) n = 1 Tax = *Hordeum vulgare* RepID = Q94IM7_HORVU (1e−54); GO_MF:GO:0015662, ATPase activity, coupled to transmembrane movement of ions, phosphorylative mechanism# (1e−54); GO_BP:GO:0015662, ATPase activity, coupled to transmembrane movement of ions, phosphorylative mechanism# (1e−54); GO_CC:GO:0016021, integral to membrane# (1e−54) | 10 | 10.1 | 3381542 | 3385865 |
| 76 | Rust resistance protein n = 7 Tax = *Zea mays* RepID = Q6PT59_MAIZE (0.0); GO_MF:GO:0005524, ATP binding# (0.0); GO_BP:GO:0006952, defense response# (0.0) | 10 | 10.1 | 3401150 | 3402412 |
| 77 | Putative reverse transcriptase n = 1 Tax = *Oryza sativa Japonica* Group RepID = Q6AU30_ORYSJ (2e−11); GO_MF:GO:0008234, cysteine-type peptidase activity# (0.0); GO_BP:GO:0006508, proteolysis# (0.0) | 10 | 10.3 | 3431811 | 3434706 |
| 78 | OSJNBa0028I23.15 protein n = 1 Tax = *Oryza sativa Japonica* Group RepID = Q7XMG7_ORYSJ (4e−15); GO_MF:GO:0003964, RNA-directed DNA polymerase, group II intron encoded# (4e−15); GO_BP:GO:0006278, RNA-dependent DNA replication# (4e−15) | 10 | 10.6 | 3539204 | 3539414 |
| 79 | Putative gag-pol polyprotein n = 1 Tax = *Zea mays* RepID = Q8SA91_MAIZE (9e−20); GO_MF:GO:0004190, penicillopepsin activity# (9e−20); GO_BP:GO:0015074, DNA integration# (9e−20); GO_CC:GO:0005634, nucleus# (9e−20) | 10 | 10.65 | 3540867 | 3543182 |
| 80 | Rust resistance protein n = 7 Tax = *Zea mays* RepID = Q6PT59_MAIZE (0.0); NB-ARC: NB-ARC domain (1.5e−46); NACHT: NACHT domain (0.013); zf-CCHC: Zinc knuckle (0.048); LRR_1: Leucine Rich Repeat (13); LRR_1: Leucine Rich Repeat (8.3); LRR_1: Leucine Rich Repeat (2.4e+02); LRR_1: Leucine Rich Repeat (31); LRR_1: Leucine Rich Repeat (35); LRR_1: Leucine Rich Repeat (2.4e+02); LRR_1: Leucine Rich Repeat (38); LRR_1: Leucine Rich Repeat (1.6e+02); LRR_1: Leucine Rich Repeat (0.75); GO_MF:GO:0005524, ATP binding# (0.0); GO_BP:GO:0006952, defense response# (0.0) | 10 | 10.75 | 3568366 | 3588140 |
| 81 | Rust resistance protein n = 7 Tax = *Zea mays* RepID = Q6PT59_MAIZE (0.0); LRR_1: Leucine Rich Repeat (13); LRR_1: Leucine Rich Repeat (5.1); LRR_1: Leucine Rich Repeat (12); LRR_1: Leucine Rich Repeat (1.5e+02); GO_MF:GO:0005524, ATP binding# (0.0); GO_BP:GO:0006952, defense response# (0.0) | 10 | 11 | 3643618 | 3645249 |
| 82 | Rust resistance protein n = 7 Tax = *Zea mays* RepID = Q6PT59_MAIZE (0.0); NB-ARC: NB-ARC domain (4.1e−36); GO_MF:GO:0005524, ATP binding# (0.0); GO_BP:GO:0006952, defense response# (0.0) | 10 | 11 | 3646298 | 3647368 |
| 83 | Rust resistance protein n = 7 Tax = *Zea mays* RepID = Q6PT59_MAIZE (0.0); GO_MF:GO:0005524, ATP binding# (0.0); GO_BP:GO:0006952, defense response# (0.0) | 10 | 11.15 | 3684166 | 3685638 |
| 84 | Rust resistance protein n = 7 Tax = *Zea mays* RepID = Q6PT59_MAIZE (0.0); NB-ARC: NB-ARC domain (2e−51); NACHT: NACHT domain (0.0049); LRR_1: Leucine Rich Repeat (13); LRR_1: Leucine Rich Repeat (2.1e+02); LRR_1: Leucine Rich Repeat (5.1); LRR_1: Leucine Rich Repeat (19); LRR_1: Leucine Rich Repeat (18); LRR_1: Leucine Rich Repeat (1.1e+02); LRR_1: Leucine Rich Repeat (64); LRR_1: Leucine Rich Repeat (0.75); GO_MF:GO:0005524, ATP binding# (0.0); GO_BP:GO:0006952, defense response# (0.0) | 10 | 11.2 | 3698037 | 3703118 |
| 85 | Putative uncharacterized protein n = 1 Tax = *Zea mays* RepID = C4JBY1_MAIZE (9e−86) | 10 | 11.3 | 3713901 | 3715447 |
| 86 | Rust resistance protein n = 7 Tax = *Zea mays* RepID = Q6PT59_MAIZE (0.0); LRR_1: Leucine Rich Repeat (13); LRR_1: Leucine Rich Repeat (5.1); LRR_1: Leucine Rich Repeat (19); LRR_1: Leucine Rich Repeat (35); LRR_1: Leucine | 10 | 11.4 | 3764373 | 3767490 |

TABLE 16-continued

Candidate genes within TARSC-10.01 interval.

| Gene ID | Annotation | Chr | MON Map cM † | Physical Map Position bp †† Start | End |
|---|---|---|---|---|---|
|  | Rich Repeat (1.1e+02); LRR_1: Leucine Rich Repeat (4); GO_MF:GO:0005524, ATP binding# (0.0); GO_BP:GO:0006952, defense response# (0.0) |  |  |  |  |
| 87 | Rust resistance protein Rp1-dp3 n = 4 Tax = *Zea mays* RepID = Q9AXD5_MAIZE (0.0); NB-ARC: NB-ARC domain (1.5e-46); NACHT: NACHT domain (0.013); GO_MF:GO:0005524, ATP binding# (0.0); GO_BP:GO:0006952, defense response# (0.0) | 10 | 11.5 | 3781509 | 3790715 |
| 88 | Rust resistance-like protein RP1-4 n = 3 Tax = *Zea mays* RepID = Q8S453_MAIZE (0.0); NB-ARC: NB-ARC domain (3e-49); NACHT: NACHT domain (0.001); LRR_1: Leucine Rich Repeat (2.2); LRR_1: Leucine Rich Repeat (13); LRR_1: Leucine Rich Repeat (14); LRR_1: Leucine Rich Repeat (70); LRR_1: Leucine Rich Repeat (75); LRR_1: Leucine Rich Repeat (9.5); GO_MF:GO:0005524, ATP binding# (0.0); GO_BP:GO:0006952, defense response# (0.0) | 10 | 11.7 | 3846913 | 3851277 |
| 89 | Helicase, putative n = 1 Tax = *Ricinus communis* RepID = B9TAC5_RICCO (3e-43); GO_MF:GO:0046872, metal ion binding# (2e-56); GO_BP:GO:0016568, chromatin modification# (3e-41); GO_CC:GO:0005634, nucleus# (3e-41) | 10 | 11.8 | 3867285 | 3869029 |
| 90 | Tobamovirus multiplication 3 n = 2 Tax = *Zea mays* RepID = B6TCL4_MAIZE (7e-25); CRAL_TRIO_N: CRAL/TRIO, N-terminus (8.8e-05); GO_MF:GO:0005215, transporter activity# (1e-23); GO_BP:GO:0006810, transport# (1e-23); GO_CC:GO:0005622, intracellular# (1e-23) | 10 | 11.8 | 3863138 | 3865019 |
| 91 | Rust resistance protein Rp1-dp3 n = 4 Tax = *Zea mays* RepID = Q9AXD5_MAIZE (0.0); NB-ARC: NB-ARC domain (1.1e-47); NACHT: NACHT domain (0.0028); LRR_1: Leucine Rich Repeat (3.3); LRR_1: Leucine Rich Repeat (11); LRR_1: Leucine Rich Repeat (2.5e+02); LRR_1: Leucine Rich Repeat (83); LRR_1: Leucine Rich Repeat (29); LRR_1: Leucine Rich Repeat (40); LRR_1: Leucine Rich Repeat (32); LRR_1: Leucine Rich Repeat (10); LRR_1: Leucine Rich Repeat (6.8); GO_MF:GO:0005524, ATP binding# (0.0); GO_BP:GO:0006952, defense response# (0.0); GO_CC:GO:0031224, intrinsic to membrane# (5e-79) | 10 | 11.9 | 3904015 | 3908862 |
| 92 | Pentatricopeptide repeat-containing protein, putative n = 1 Tax = *Ricinus communis* RepID = B9T5G9_RICCO (0.0); PPR: PPR repeat (4.7); PPR: PPR repeat (2.2e-08); PPR: PPR repeat (0.00083); PPR: PPR repeat (7.7e-06); PPR: PPR repeat (3.1e-06); PPR: PPR repeat (1); PPR: PPR repeat (4.3e-10); PPR: PPR repeat (1.1e-11); PPR: PPR repeat (1.6); WRKY: WRKY DNA -binding domain (5.6e-21); GO_MF:GO:0005488, binding# (0.0); GO_CC:GO:0005739, mitochondrion# (1e-140) | 10 | 12.2 | 3987414 | 3993918 |
| 93 | Rust resistance protein Rp1-dp3 n = 4 Tax = *Zea mays* RepID = Q9AXD5_MAIZE (0.0); Fucokinase: L-fucokinase (0.07); NB-ARC: NB-ARC domain (7.9e-48); NACHT: NACHT domain (0.0042); LRR_1: Leucine Rich Repeat (3e+02); LRR_1: Leucine Rich Repeat (1.1); LRR_1: Leucine Rich Repeat (1.9); LRR_1: Leucine Rich Repeat (18); LRR_1: Leucine Rich Repeat (63); LRR_1: Leucine Rich Repeat (30); LRR_1: Leucine Rich Repeat (83); LRR_1: Leucine Rich Repeat (2.6e+02); LRR_1: Leucine Rich Repeat (2.9e+02); LRR_1: Leucine Rich Repeat (4.5); GO_MF:GO:0005524, ATP binding# (0.0); GO_BP:GO:0006952, defense response# (0.0) | 10 | 12.2 | 3980758 | 3986845 |
| 94 | Putative uncharacterized protein Sb03g035710 n = 1 Tax = *Sorghum bicolor* RepID = C5XKY5_SORBI (3e-49); GO_MF:GO:0046983, protein dimerization activity# (7e-15) | 10 | 12.4 | 4014579 | 4015124 |
| 95 | SET domain protein n = 1 Tax = *Populus trichocarpa* RepID = B9GPK5_POPTR (1e-100); SET: SET domain (2.3e-51); GO_MF:GO:0016740, transferase activity# (1e-125); GO_BP:GO:0051568, IMP#histone H3-K4 methylation# (7e-89); GO_CC:GO:0005634, nucleus# (1e-125) | 10 | 12.4 | 4015955 | 4019522 |
| 96 | RHC1A n = 3 Tax = Andropogoneae RepID = B6T7M2_MAIZE (3e-11); zf-C3HC4: Zinc finger, C3HC4 type (RING finger) (1.5e-08); GO_MF:GO:0046872, metal ion binding# (4e-14); GO_BP:GO:0006355, regulation of transcription, DNA-dependent# (6e-10); GO_CC:GO:0005634, nucleus# (6e-10) | 10 | 12.5 | 4024203 | 4024796 |
| 97 | WRKY transcription factor 64-like protein n = 2 Tax = *Oryza sativa* RepID = Q6H4S7_ORYSJ (8e-14); WRKY: WRKY DNA -binding domain (0.00015); GO_MF:GO:0043565, sequence-specific DNA binding# (1e-48); GO_BP:GO:0045449, regulation of transcription# (1e-48); GO_CC:GO:0005634, nucleus# (1e-48) | 10 | 12.5 | 4032506 | 4034316 |

TABLE 16-continued

Candidate genes within TARSC-10.01 interval.

| Gene ID | Annotation | Chr | MON Map cM † | Physical Map Position bp †† Start | End |
|---|---|---|---|---|---|
| 98 | Elongation factor P n = 2 Tax = Andropogoneae RepID = B6UC94_MAIZE (1e−109); EFP_N: Elongation factor P (EF-P) KOW-like do (1.2e−29); EFP: Elongation factor P (EF-P) (3.9e−23); Elong-fact-P_C: Elongation factor P, C-terminal (4.4e−26); GO_MF:GO:0003746, protein-synthesizing GTPase activity, elongation# (1e−109); GO_BP:GO:0006414, translational elongation# (1e−109); GO_CC:GO:0005737, cytoplasm# (1e−109) | 10 | 12.7 | 4071262 | 4073878 |
| 99 | OSIGBa0113E10.15 protein n = 2 Tax = *Oryza sativa* RepID = Q00RP1_ORYSA (2e−11); DUF2076: Uncharacterized protein conserved in b (0.074); DUF2457: Protein of unknown function (DUF2457) (0.069); GO_MF:GO:0016758, transferase activity, transferring hexosyl groups# (8e−16); GO_BP:GO:0008152, metabolic process# (8e−16); GO_CC:GO:0016020, membrane# (5e−11) | 10 | 12.7 | 4052643 | 4059970 |
| 100 | OSIGBa0113E10.15 protein n = 2 Tax = *Oryza sativa* RepID = Q00RP1_ORYSA (4e−18); Peptidase_C65: Peptidase C65 Otubain (8.5e−08); GO_MF:GO:00 16787, hydrolase activity# (4e−13); GO_BP:GO:0006519, cellular amino acid and derivative metabolic process# (4e−13) | 10 | 12.7 | 4064804 | 4070919 |
| 101 | Putative retroelement protein n = 1 Tax = *Sorghum bicolor* RepID = B3VTB4_SORBI (2e−12); GO_MF:GO:0003964, RNA-directed DNA polymerase, group II intron encoded# (7e−11); GO_BP:GO:0006355, regulation of transcription, DNA-dependent# (2e−12); GO_CC:GO:0005634, nucleus# (2e−12) | 10 | 12.7 | 4063108 | 4063916 |
| 102 | Major facilitator superfamily antiporter n = 1 Tax = *Oryza sativa Japonica* Group RepID = Q8H6D6_ORYSJ (9e−58); GO_MF:GO:0015520, tetracycline:hydrogen antiporter activity# (1e−38); GO_BP:GO:0055085, transmembrane transport# (9e−58); GO_CC:GO:0016021, integral to membrane# (1e−38) | 10 | 13.1 | 4157290 | 4162170 |
| 103 | Non-specific lipid-transfer protein n = 21 Tax = *Zea* RepID = NLTP_MAIZE (2e−34); Tryp_alpha_amyl: Protease inhibitor/seed storage/LTP f (1.8e−32); GO_MF:GO:0008289, lipid binding# (2e−34); GO_BP:GO:0006869, lipid transport# (2e−34) | 10 | 13.1 | 4165993 | 4166453 |
| 104 | Putative uncharacterized protein Sb08g002730 n = 1 Tax = *Sorghum bicolor* RepID = C5YRL9_SORBI (4e−97); DUF641: Plant protein of unknown function (DUF641) (0.005) | 10 | 13.6 | 4287564 | 4288746 |
| 105 | Putative uncharacterized protein Sb08g002730 n = 1 Tax = *Sorghum bicolor* RepID = C5YRL9_SORBI (6e−45); DUF641: Plant protein of unknown function (DUF641) (2.4e−12) | 10 | 13.7 | 4307780 | 4308368 |
| 106 | Transposon protein, putative, CACTA, En/Spm sub-class n = 1 Tax = *Oryza sativa Japonica* Group RepID = Q2R1M9_ORYSJ (2e−35); GO_MF:GO:0004803, transposase activity# (1e−48); GO_BP:GO:0006313, transposition, DNA-mediated# (1e−48) | 10 | 13.7 | 4309780 | 4315068 |
| 107 | CBL-interacting protein kinase 02 n = 1 Tax = *Sorghum bicolor* RepID = C4P7T9_SORBI (0.0); Pkinase: Protein kinase domain (9.1e−92); Pkinase_Tyr: Protein tyrosine kinase (1.1e−24); NAF: NAF domain (2.5e−26); GO_MF:GO:0016740, transferase activity# (0.0); GO_BP:GO:0016301, kinase activity# (0.0) | 10 | 13.8 | 4393509 | 4396185 |
| 108 | Mevalonate kinase n = 4 Tax = Andropogoneae RepID = B6UAN3_MAIZE (5e−25); GO_MF:GO:0016773, phosphotransferase activity, alcohol group as acceptor# (5e−25); GO_BP:GO:0016310, hyperphosphorylation# (5e−25); GO_CC:GO:0005737, cytoplasm# (5e−25) | 10 | 13.8 | 4386241 | 4388108 |
| 109 | MURAZC n = 2 Tax = *Zea mays* RepID = P93802_MAIZE (5e−09); zf-CCHC: Zinc knuckle (0.021); GO_MF:GO:0008270, zinc ion binding# (5e−09); GO_BP:GO:0006313, transposition, DNA-mediated# (5e−09) | 10 | 13.8 | 4396544 | 4397204 |
| 110 | Putative uncharacterized protein Sb03g004110 n = 1 Tax = *Sorghum bicolor* RepID = C5XMT7_SORBI (7e−39) | 10 | 13.8 | 4386268 | 4386582 |
| 111 | Putative unclassified retrotransposon protein n = 1 Tax = *Oryza sativa Indica* Group RepID = C5NNP0_ORYSI (0.0); Zea_mays_MuDR: *Zea mays* MURB-like protein (MuDR) (1.8e−90); zf-CCHC: Zinc knuckle (0.0028); Exo_endo_phos: Endonuclease/Exonuclease/phosphalase family (9e−05); GO_MF:GO:0003964, RNA-directed DNA polymerase, group II intron encoded# (1e−168); GO_BP:GO:0006278, RNA-dependent DNA replication# (1e−168) | 10 | 13.8 | 4400220 | 4405960 |
| 112 | CBL-interacting protein kinase 02 n = 1 Tax = *Sorghum bicolor* RepID = C4P7T9_SORBI (0.0); Pkinase: Protein kinase domain (9.4e−93); Pkinase_Tyr: Protein tyrosine kinase (1.9e−24); NAF: NAF domain (2.5e−26); GO_MF:GO:0016740, transferase activity# (0.0); GO_BP:GO:0016301, kinase activity# (0.0) | 10 | 13.9 | 4467656 | 4468987 |

TABLE 16-continued

Candidate genes within TARSC-10.01 interval.

| Gene ID | Annotation | Chr | MON Map cM † | Physical Map Position bp †† Start | End |
|---|---|---|---|---|---|
| 113 | PHD-type zinc finger protein-like n = 1 Tax = *Oryza sativa Japonica* Group RepID = Q84NP5_ORYSJ (2e−87); PRONE: PRONE (Plant-specific Rop nucleotide exc (2.2e−09); PHD: PHD-finger (8.1e−12); Acetyltransf_1: Acetyltransferase (GNAT) family (0.0026); GO_MF:GO:0046872, metal ion binding# (2e−87); GO_BP:GO:0008152, metabolic process# (2e−87) | 10 | 13.9 | 4446649 | 4455684 |
| 114 | Putative gag-pol polyprotein n = 1 Tax = *Zea mays* RepID = Q8SA91_MAIZE (6e−18); GO_MF:GO:0004190, penicillopepsin activity# (6e−18); GO_BP:GO:0015074, DNA integration# (6e−18); GO_CC:GO:0005634, nucleus# (6e−18) | 10 | 13.9 | 4480868 | 4481164 |
| 115 | Arginine decarboxylase, putative n = 1 Tax = *Ricinus communis* RepID = B9SJR9_RICCO (2e−63); OKR_DC_1: Orn/Lys/Arg decarboxylase, major domain (8.2e−07); GO_MF:GO:0030170, pyridoxal phosphate binding# (1e−115); GO_BP:GO:0003993, acid phosphatase activity# (5e−87); GO_CC:GO:0005737, cytoplasm# (4e−28) | 10 | 14 | 4514835 | 4515804 |
| 116 | ATP binding protein n = 1 Tax = *Zea mays* RepID = B6TPV9_MAIZE (7e−69); GO_MF:GO:0046872, metal ion binding# (1e−33); GO_BP:GO:0006355, regulation of transcription, DNA-dependent# (1e−33) | 10 | 14 | 4510518 | 4513154 |
| 117 | CBL-interacting protein kinase 02 n = 1 Tax = *Sorghum bicolor* RepID = C4P7T9_SORBI (0.0); Pkinase_Tyr: Protein tyrosine kinase (3.1e−22); Pkinase: Protein kinase domain (2.2e−93); NAF: NAF domain (5.8e−26); GO_MF:GO:0016740, transferase activity# (0.0); GO_BP:GO:0016301, kinase activity# (0.0) | 10 | 14 | 4524581 | 4526322 |
| 118 | Peptidyl-prolyl cis-trans isomerase n = 3 Tax = Andropogoneae RepID = C5X6M4_SORBI (8e−39); Pro_isomerase: Cyclophilin type peptidyl-prolyl cis-tr (1.3e−33); GO_MF:GO:0016853, isomerase activity# (6e−38); GO_BP:GO:0006457, protein folding# (6e−38); GO_CC:GO:0005737, cytoplasm# (3e−34) | 10 | 14 | 4516263 | 4516797 |
| 119 | Putative uncharacterized protein Sb08g002750 n = 2 Tax = Andropogoneae RepID = C5YRM4_SORBI (7e−40) | 10 | 14 | 4527499 | 4528270 |
| 120 | Putative uncharacterized protein Sb08g002760 n = 1 Tax = *Sorghum bicolor* RepID = C5YRM5_SORBI (0.0); TFIIB_Zn_Ribbon: TFIIB zinc-binding (0.028); TolA: TolA protein (0.078); MAP7: MAP7 (E-MAP-115) family (0.1) | 10 | 14.1 | 4558210 | 4565120 |
| 121 | RNA-binding protein 12 n = 3 Tax = *Zea mays* RepID = B6TFP1_MAIZE (9e−80); Tryp_alpha_amyl: Protease inhibitor/seed storage/LTP f (0.00072); GO_BP:GO:0006869, lipid transport# (1e−09) | 10 | 14.6 | 4584387 | 4586255 |
| 122 | Major facilitator superfamily MFS_1 n = 1 Tax = *Pseudomonas mendocina* ymp RepID = A4XSH8_PSEMY (1e−37); TLC: TLC ATP/ADP transporter (0.0083); GO_BP:GO:0055085, transmembrane transport# (2e−42) | 10 | 15.2 | 4586332 | 4592954 |
| 123 | Surfactant protein B containing protein n = 3 Tax = *Zea mays* RepID = B6T692_MAIZE (1e−114); SapB_1: Saposin-like type B, region 1 (0.003); SapB_2: Saposin-like type B, region 2 (0.0016); SapB_1: Saposin-like type B, region 1 (6.4e−05); SapB_2: Saposin-like type B, region 2 (1.2e−05); GO_MF:GO:0008289, lipid binding# (6e−09); GO_BP:GO:0006629, lipid metabolic process# (1e−114); GO_CC:GO:0005764, lysosome# (2e−36) | 10 | 15.2 | 4592397 | 4594115 |
| 124 | Chloroplast-targeted copper chaperone, putative n = 1 Tax = *Ricinus communis* RepID = B9RTT9_RICCO (2e−26); HMA: Heavy-metal-associated domain (3.4e−11); GO_MF:GO:0046872, metal ion binding# (4e−34); GO_BP:GO:0030001, metal ion transport# (4e−34); GO_CC:GO:0005618, IDA#cell wall# (1e−24) | 10 | 15.35 | 4611629 | 4615022 |
| 125 | Retrotransposon protein, putative, unclassified n = 1 Tax = *Oryza sativa Japonica* Group RepID = Q2RAL0_ORYSJ (0.0); zf-CCHC: Zinc knuckle (0.0028); Exo_endo_phos: Endonuclease/Exonuclease/phosphatase family (6.5e−05); RVT_1: Reverse transcriptase (RNA-dependent DN (2.7e−21); GO_MF:GO:0003964, RNA-directed DNA polymerase, group II intron encoded# (0.0); GO_BP:GO:0006278, RNA-dependent DNA replication# (0.0); GO_CC:GO:0000145, NAS#exocyst# (1e−175) | 10 | 15.6 | 4651214 | 4658099 |
| 126 | Nucleolus protein required for cell viability, putative n = 1 Tax = *Talaromyces stipitatus* ATCC 10500 RepID = B8LVD6_TALSN (5e−56); DEAD: DEAD/DEAH box helicase (0.023); DUF1253: Protein of unknown function (DUF1253) (6.9e−28); GO_BP:GO:0007275, TAS#multicellular organismal development# (2e−53); GO_CC:GO:0005634, nucleus# (2e−53) | 10 | 15.7 | 4640408 | 4664484 |

TABLE 16-continued

Candidate genes within TARSC-10.01 interval.

| Gene ID | Annotation | Chr | MON Map cM † | Physical Map Position bp †† Start | End |
|---|---|---|---|---|---|
| 127 | Prenyl-dependent CAAX protease, putative n = 1 Tax = *Ricinus communis* RepID = B9RMQ5_RICCO (1e-57); Abi: CAAX amino terminal protease family (4e-18); GO_MF:GO:0008233, peptidase activity# (1e-57); GO_CC:GO:0016020, membrane# (3e-80) | 10 | 16 | 4664877 | 4667695 |
| 128 | Acyl-CoA binding protein n = 3 Tax = Andropogoneae RepID = B6U8G5_MAIZE (2e-20); GO_MF:GO:0005515, protein binding# (2e-20); GO_BP:GO:0009753, IEP#response to jasmonic acid stimulus# (7e-13); GO_CC:GO:0005829, IDA#cytosol# (7e-13) | 10 | 16.35 | 4669916 | 4671356 |
| 129 | Aluminum-induced protein n = 1 Tax = *Elaeis guineensis* RepID = B3TLT4_ELAGV (1e-107); GO_CC:GO:0005829, IDA#cytosol# (9e-48) | 10 | 16.65 | 4673461 | 4676134 |

† cM = centiMorgans.
†† bp = base pair of Arizona Genomics Institute B73 RefGen_v2 sequence.

As various modifications could be made in the constructions and methods herein described and illustrated without departing from the scope of the invention, it is intended that all matter contained in the foregoing description or shown in the accompanying drawings shall be interpreted as illustrative rather than limiting. The breadth and scope of the present invention should not be limited by any of the above-described exemplary embodiments, but should be defined only in accordance with the following claims appended hereto and their equivalents. All patent and non-patent documents cited in this specification are incorporated herein by reference in their entireties.

What is claimed is:

1. A method of obtaining a corn plant with improved tar spot complex (TARSC) resistance, said method comprising:
   a) providing a population of corn plants;
   b) obtaining at least one DNA sample from at least one plant within said population;
   c) detecting in the DNA sample the presence of a TARSC resistance allele comprising a "T" at nucleotide position 61 of SEQ ID NO: 6 in, or genetically linked to, a chromosomal segment between about 3.99 cM and about 17.7 cM on chromosome 10;
   d) selecting one or more plants from said population based on the presence of said allele;
   e) crossing at least one selected plant comprising said allele with a second corn plant that comprises one or zero TARSC resistance alleles to produce one or more progeny plants that produce seeds;
   f) collecting the seeds produced by the one or more progeny plants; and
   g) growing from said seeds at least one plant having said allele and having improved TARSC resistance.

2. The method of claim 1, wherein said segment is flanked by loci SEQ ID NO: 1 and SEQ ID NO: 7 on chromosome 10.

3. The method of claim 2, wherein said segment is flanked by loci SEQ ID NO: 4 and SEQ ID NO: 6 on chromosome 10.

4. The method of claim 1, wherein said segment is located between about 9.4 cM and about 13.7 cM, or between about 8.3 cM and about 11.9 cM on chromosome 10.

5. The method of claim 1, wherein said chromosomal segment comprises the sequence of SEQ ID NO: 1.

6. The method of claim 1, wherein said plant exhibits increased yield relative to a control plant not comprising said TARSC resistance allele.

7. The method of claim 1, wherein step (a) of providing comprises crossing a first corn plant comprising a TARSC resistance allele with a second corn plant to produce a population of corn plants.

8. The method of claim 7, wherein producing the population of corn plants comprises backcrossing.

9. The method of claim 1, wherein step (c) of detecting comprises the use of an oligonucleotide probe.

10. A method of producing a corn plant with improved tar spot complex (TARSC) resistance, said method comprising:
    a) crossing a first corn plant comprising a TARSC resistance allele with a second corn plant of a different genotype to produce one or more progeny plants;
    b) obtaining at least one DNA sample from at least one progeny plant;
    c) detecting the presence of said allele comprising a "T" at nucleotide position 61 of SEQ ID NO: 6 in, or genetically linked to, a chromosomal segment between about 3.99 cM and about 17.7 cM on chromosome 10 in the DNA sample;
    d) selecting one or more progeny plants based on the presence of said allele; wherein said allele confers improved TARSC resistance compared to a plant lacking said allele e) collecting seeds produced by the one or more progeny plants; and
    f) growing from said seeds at least one plant having said allele and having improved TARSC resistance.

11. The method of claim 10, wherein said segment is flanked by loci SEQ ID NO: 1 and SEQ ID NO: 7 on chromosome 10.

12. The method of claim 11, wherein said segment is flanked by loci SEQ ID NO: 4 and SEQ ID NO: 6 on chromosome 10.

13. The method of claim 10, wherein said segment is located between about between about 9.4 cM and about 13.7 cM, or between about 8.3 cM and about 11.9 cM on chromosome 10.

14. The method of claim 10, wherein said chromosomal segment comprises the sequence of SEQ ID NO: 1.

15. The method of claim 10, wherein said plant exhibits increased yield relative to a control plant not comprising said TARSC resistance allele.

16. The method of claim 10, further comprising:
    g) crossing said progeny plant with itself or a second plant to produce one or more further progeny plants; and
    h) selecting a further progeny plant comprising said allele.

17. The method of claim 16, wherein step (h) of selecting comprises marker-assisted selection.

18. The method of claim 17, wherein said marker-assisted selection comprises selecting a progeny plant based on the presence of said allele in the sequence of SEQ ID NO:6.

19. The method of claim 16, wherein said further progeny plant is an F2-F7 progeny plant.

20. The method of claim 19, wherein producing the progeny plant comprises backcrossing.

21. The method of claim 20, wherein backcrossing comprises from 2-7 generations of backcrosses.

22. The method of claim 20, wherein backcrossing comprises marker-assisted selection.

23. The method of claim 22, wherein backcrossing comprises marker-assisted selection in at least two generations.

24. The method of claim 23, wherein backcrossing comprises marker-assisted selection in all generations.

25. The method of claim 22, wherein said marker-assisted selection comprises selecting a progeny plant based on the presence of said allele in a polymorphic locus that comprises the sequence of SEQ ID NO: 1.

26. The method of claim 10, wherein said first corn plant is an inbred or a hybrid.

27. The method of claim 10, wherein said second corn plant is an agronomically elite corn plant.

28. The method of claim 27, wherein said agronomically elite corn plant is an inbred or a hybrid.

29. The method of claim 1, wherein said chromosomal segment comprises the sequence of SEQ ID NO: 2.

30. The method of claim 1, wherein said chromosomal segment comprises the sequence of SEQ ID NO: 3.

31. The method of claim 1, wherein said chromosomal segment comprises the sequence of SEQ ID NO: 4.

32. The method of claim 1, wherein said chromosomal segment comprises the sequence of SEQ ID NO: 5.

33. The method of claim 1, wherein said chromosomal segment comprises the sequence of SEQ ID NO: 6.

34. The method of claim 1, wherein said chromosomal segment comprises the sequence of SEQ ID NO: 7.

35. The method of claim 1, wherein said chromosomal segment comprises the sequence of SEQ ID NO: 36.

36. The method of claim 10, wherein said chromosomal segment comprises the sequence of SEQ ID NO: 2.

37. The method of claim 10, wherein said chromosomal segment comprises the sequence of SEQ ID NO: 3.

38. The method of claim 10, wherein said chromosomal segment comprises the sequence of SEQ ID NO: 4.

39. The method of claim 10, wherein said chromosomal segment comprises the sequence of SEQ ID NO: 5.

40. The method of claim 10, wherein said chromosomal segment comprises the sequence of SEQ ID NO: 6.

41. The method of claim 10, wherein said chromosomal segment comprises the sequence of SEQ ID NO: 7.

42. The method of claim 10, wherein said chromosomal segment comprises the sequence of SEQ ID NO: 36.

43. The method of claim 22, wherein said marker-assisted selection comprises selecting a progeny plant based on the presence of said allele in a polymorphic locus that comprises the sequence of SEQ ID NO: 2.

44. The method of claim 22, wherein said marker-assisted selection comprises selecting a progeny plant based on the presence of said allele in a polymorphic locus that comprises the sequence of SEQ ID NO: 3.

45. The method of claim 22, wherein said marker-assisted selection comprises selecting a progeny plant based on the presence of said allele in a polymorphic locus that comprises the sequence of SEQ ID NO: 4.

46. The method of claim 22, wherein said marker-assisted selection comprises selecting a progeny plant based on the presence of said allele in a polymorphic locus that comprises the sequence of SEQ ID NO: 5.

47. The method of claim 22, wherein said marker-assisted selection comprises selecting a progeny plant based on the presence of said allele in a polymorphic locus that comprises the sequence of SEQ ID NO: 6.

48. The method of claim 22, wherein said marker-assisted selection comprises selecting a progeny plant based on the presence of said allele in a polymorphic locus that comprises the sequence of SEQ ID NO: 7.

49. The method of claim 22, wherein said marker-assisted selection comprises selecting a progeny plant based on the presence of said allele in a polymorphic locus that comprises the sequence of SEQ ID NO: 36.

* * * * *

```
                     SEQUENCE LISTING

<160> NUMBER OF SEQ ID NOS: 40

<210> SEQ ID NO 1
<211> LENGTH: 121
<212> TYPE: DNA
<213> ORGANISM: Zea mays
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc_feature
<222> LOCATION: (20)..(20)
<223> OTHER INFORMATION: n is a, c, g, or t
<220> FEATURE:
<221> NAME/KEY: misc_feature
<222> LOCATION: (55)..(55)
<223> OTHER INFORMATION: n is a, c, g, or t
<220> FEATURE:
<221> NAME/KEY: misc_feature
<222> LOCATION: (61)..(61)
<223> OTHER INFORMATION: n is a, c, g, or t

<400> SEQUENCE: 1
tacnaaaagt cgcatgttcn aactctgttt tctctgcact aacttcctta tcttnaaata     60
ntatgcatta ccatgtataa cacactcgca catgtgtgtg aacctgcaca tgaaaacatc    120
a                                                                    121

<210> SEQ ID NO 2
<211> LENGTH: 121
<212> TYPE: DNA
<213> ORGANISM: Zea mays
<220> FEATURE:
<221> NAME/KEY: misc_feature
<222> LOCATION: (61)..(61)
<223> OTHER INFORMATION: n is a, c, g, or t
<220> FEATURE:
<221> NAME/KEY: misc_feature
<222> LOCATION: (115)..(115)
<223> OTHER INFORMATION: n is a, c, g, or t
```

<220> FEATURE:
<221> NAME/KEY: misc_feature
<222> LOCATION: (117)..(117)
<223> OTHER INFORMATION: n is a, c, g, or t

<400> SEQUENCE: 2
gtctagaaac attattgctc ccagtcaact atagcatctg tgctgcagaa gttctgcttc    60
ntagagggta ttgtcataat ttatacaaac ttggtgcatg tttaaacttg gtttntntat   120
t                                                                  121

<210> SEQ ID NO 3
<211> LENGTH: 194
<212> TYPE: DNA
<213> ORGANISM: Zea mays
<220> FEATURE:
<221> NAME/KEY: misc_feature
<222> LOCATION: (31)..(58)
<223> OTHER INFORMATION: n is a, c, g, or t
<220> FEATURE:
<221> NAME/KEY: misc_feature
<222> LOCATION: (94)..(115)
<223> OTHER INFORMATION: n is a, c, g, or t
<220> FEATURE:
<221> NAME/KEY: misc_feature
<222> LOCATION: (132)..(132)
<223> OTHER INFORMATION: n is a, c, g, or t
<220> FEATURE:
<221> NAME/KEY: misc_feature
<222> LOCATION: (193)..(194)
<223> OTHER INFORMATION: n is a, c, g, or t

<400> SEQUENCE: 3
ggtactatag ttggaggacg tccgttacta nnnnnnnnnn nnnnnnnnnn nnnnnnnnat    60
ttgtgctgac gcgcaagttc gaggttaaaa aaannnnnnn nnnnnnnnnn nnnnngatgt   120
tatctcgaat anatagccat tgtacttggt aggtgagata ttataagata ggtatgctat   180
gcgtgaatgg tgnn                                                    194

<210> SEQ ID NO 4
<211> LENGTH: 121
<212> TYPE: DNA
<213> ORGANISM: Zea mays
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (33)..(33)
<223> OTHER INFORMATION: n is a, c, g, or t
<220> FEATURE:
<221> NAME/KEY: misc_feature
<222> LOCATION: (61)..(61)
<223> OTHER INFORMATION: n is a, c, g, or t

<400> SEQUENCE: 4
ttnactgtcg ctgtccatca tttcttgtag ctngatgtag ctagtgctgc cttttcatcc    60
nttgaccact atacgcgcaa cccacacgct atgaagaaag tctttaatca aagcccatat   120
g                                                                  121

<210> SEQ ID NO 5
<211> LENGTH: 201
<212> TYPE: DNA
<213> ORGANISM: Zea mays
<220> FEATURE:
<221> NAME/KEY: misc_feature
<222> LOCATION: (23)..(23)

```
<223> OTHER INFORMATION: n is a, c, g, or t
<220> FEATURE:
<221> NAME/KEY: misc_feature
<222> LOCATION: (42)..(43)
<223> OTHER INFORMATION: n is a, c, g, or t
<220> FEATURE:
<221> NAME/KEY: misc_feature
<222> LOCATION: (101)..(101)
<223> OTHER INFORMATION: n is a, c, g, or t
<220> FEATURE:
<221> NAME/KEY: misc_feature
<222> LOCATION: (165)..(165)
<223> OTHER INFORMATION: n is a, c, g, or t

<400> SEQUENCE: 5
gtcccagtat atccaccatg cangcaaagt gttccagttg annaaccagt ttgtagcggc      60
ttgtcatcag atggaaatac tggcatccat cgtccagcag nccgacatgg ctgcatgccc     120
gcagaactgc gacgaaagtc gcgtggttcg gcaccacatt tgctntctgc atcctctcaa    180
acatctccag ggcttcaagt c                                                201

<210> SEQ ID NO 6
<211> LENGTH: 121
<212> TYPE: DNA
<213> ORGANISM: Zea mays
<220> FEATURE:
<221> NAME/KEY: misc_feature
<222> LOCATION: (61)..(61)
<223> OTHER INFORMATION: n is a, c, g, or t

<400> SEQUENCE: 6
ggagtagtag gctagtagct agctagctag ctggtgcgtg tcgttcgtgg atggagaaat      60
naagagagag agggagagaa tggcggtcgt tgttcggtgg aaagtggaat gtgtgaggga    120
g                                                                      121

<210> SEQ ID NO 7
<211> LENGTH: 201
<212> TYPE: DNA
<213> ORGANISM: Zea mays
<220> FEATURE:
<221> NAME/KEY: misc_feature
<222> LOCATION: (101)..(101)
<223> OTHER INFORMATION: n is a, c, g, or t
<220> FEATURE:
<221> NAME/KEY: misc_feature
<222> LOCATION: (124)..(124)
<223> OTHER INFORMATION: n is a, c, g, or t
<220> FEATURE:
<221> NAME/KEY: misc_feature
<222> LOCATION: (165)..(165)
<223> OTHER INFORMATION: n is a, c, g, or t
<220> FEATURE:
<221> NAME/KEY: misc_feature
<222> LOCATION: (170)..(170)
<223> OTHER INFORMATION: n is a, c, g, or t
<220> FEATURE:
<221> NAME/KEY: misc_feature
<222> LOCATION: (172)..(172)
<223> OTHER INFORMATION: n is a, c, g, or t

<400> SEQUENCE: 7
gattttgggt tcatttgcta gcactaaggt acataagcaa caaactgctg tgccatcaga      60
acccacaaat atgggttata cggaacaatg actggtcacg naagagcatg aagagaccac    120
cctnccaccg caggttgcaa gatggaaaca gcatggcacg ctggntagcn anattggaaa    180
cccgacgcct aggagtccca a                                                201
```

-continued

```
<210> SEQ ID NO 8
<211> LENGTH: 26
<212> TYPE: DNA
<213> ORGANISM: Zea mays

<400> SEQUENCE: 8
ctctgttttc tctgcactaa cttcct                                              26

<210> SEQ ID NO 9
<211> LENGTH: 24
<212> TYPE: DNA
<213> ORGANISM: Zea mays

<400> SEQUENCE: 9
gctcccagtc aactatagca tctg                                                24

<210> SEQ ID NO 10
<211> LENGTH: 21
<212> TYPE: DNA
<213> ORGANISM: Zea mays

<400> SEQUENCE: 10
cgcgcaagtt cgaggttaaa a                                                   21

<210> SEQ ID NO 11
<211> LENGTH: 24
<212> TYPE: DNA
<213> ORGANISM: Zea mays

<400> SEQUENCE: 11
cgctgtccat catttcttgt agct                                                24

<210> SEQ ID NO 12
<211> LENGTH: 24
<212> TYPE: DNA
<213> ORGANISM: Zea mays

<400> SEQUENCE: 12
gcggcttgtc atcagatgga aata                                                24

<210> SEQ ID NO 13
<211> LENGTH: 18
<212> TYPE: DNA
<213> ORGANISM: Zea mays

<400> SEQUENCE: 13
tgcgtgtcgt tcgtggat                                                       18

<210> SEQ ID NO 14
<211> LENGTH: 24
<212> TYPE: DNA
<213> ORGANISM: Zea mays

<400> SEQUENCE: 14
gtgccatcag aacccacaaa tatg                                                24

<210> SEQ ID NO 15
<211> LENGTH: 20
<212> TYPE: DNA
<213> ORGANISM: Zea mays

<400> SEQUENCE: 15
tcacacacat gtgcgagtgt                                                     20
```

```
<210> SEQ ID NO 16
<211> LENGTH: 26
<212> TYPE: DNA
<213> ORGANISM: Zea mays

<400> SEQUENCE: 16
aaaccaagtt taaacatgca ccaagt                                          26

<210> SEQ ID NO 17
<211> LENGTH: 28
<212> TYPE: DNA
<213> ORGANISM: Zea mays

<400> SEQUENCE: 17
ccattcacgc atagcatacc tatcttat                                        28

<210> SEQ ID NO 18
<211> LENGTH: 19
<212> TYPE: DNA
<213> ORGANISM: Zea mays

<400> SEQUENCE: 18
gtgtgggttg cgcgtatag                                                  19

<210> SEQ ID NO 19
<211> LENGTH: 17
<212> TYPE: DNA
<213> ORGANISM: Zea mays

<400> SEQUENCE: 19
agttctgcgg gcatgca                                                    17

<210> SEQ ID NO 20
<211> LENGTH: 20
<212> TYPE: DNA
<213> ORGANISM: Zea mays

<400> SEQUENCE: 20
aacaacgacc gccattctct                                                 20

<210> SEQ ID NO 21
<211> LENGTH: 22
<212> TYPE: DNA
<213> ORGANISM: Zea mays

<400> SEQUENCE: 21
tgctgtttcc atcttgcaac ct                                              22

<210> SEQ ID NO 22
<211> LENGTH: 19
<212> TYPE: DNA
<213> ORGANISM: Zea mays

<400> SEQUENCE: 22
atggtaatgc ataatattt                                                  19

<210> SEQ ID NO 23
<211> LENGTH: 18
<212> TYPE: DNA
<213> ORGANISM: Zea mays

<400> SEQUENCE: 23
ataccctcta agaagcag                                                   18
```

<210> SEQ ID NO 24
<211> LENGTH: 17
<212> TYPE: DNA
<213> ORGANISM: Zea mays

<400> SEQUENCE: 24
caatggctat gtattcg                                                    17

<210> SEQ ID NO 25
<211> LENGTH: 21
<212> TYPE: DNA
<213> ORGANISM: Zea mays

<400> SEQUENCE: 25
tgccttttca tcctttgacc a                                               21

<210> SEQ ID NO 26
<211> LENGTH: 15
<212> TYPE: DNA
<213> ORGANISM: Zea mays

<400> SEQUENCE: 26
cagcaggccg acatg                                                      15

<210> SEQ ID NO 27
<211> LENGTH: 18
<212> TYPE: DNA
<213> ORGANISM: Zea mays

<400> SEQUENCE: 27
ctctctctct taatttct                                                   18

<210> SEQ ID NO 28
<211> LENGTH: 16
<212> TYPE: DNA
<213> ORGANISM: Zea mays

<400> SEQUENCE: 28
actggtcacg gaagag                                                     16

<210> SEQ ID NO 29
<211> LENGTH: 19
<212> TYPE: DNA
<213> ORGANISM: Zea mays

<400> SEQUENCE: 29
atggtaatgc atagtattt                                                  19

<210> SEQ ID NO 30
<211> LENGTH: 16
<212> TYPE: DNA
<213> ORGANISM: Zea mays

<400> SEQUENCE: 30
accctctagg aagcag                                                     16

<210> SEQ ID NO 31
<211> LENGTH: 17
<212> TYPE: DNA
<213> ORGANISM: Zea mays

<400> SEQUENCE: 31

```
caatggctat atattcg                                                        17

<210> SEQ ID NO 32
<211> LENGTH: 19
<212> TYPE: DNA
<213> ORGANISM: Zea mays

<400> SEQUENCE: 32
ccttttcatc ccttgacca                                                      19

<210> SEQ ID NO 33
<211> LENGTH: 16
<212> TYPE: DNA
<213> ORGANISM: Zea mays

<400> SEQUENCE: 33
ccagcagacc gacatg                                                         16

<210> SEQ ID NO 34
<211> LENGTH: 18
<212> TYPE: DNA
<213> ORGANISM: Zea mays

<400> SEQUENCE: 34
ctctctctct tcatttct                                                       18

<210> SEQ ID NO 35
<211> LENGTH: 15
<212> TYPE: DNA
<213> ORGANISM: Zea mays

<400> SEQUENCE: 35
ctggtcacga aagag                                                          15

<210> SEQ ID NO 36
<211> LENGTH: 121
<212> TYPE: DNA
<213> ORGANISM: Zea mays
<220> FEATURE:
<221> NAME/KEY: misc_feature
<222> LOCATION: (24)..(24)
<223> OTHER INFORMATION: n is a, c, g, or t
<220> FEATURE:
<221> NAME/KEY: misc_feature
<222> LOCATION: (61)..(61)
<223> OTHER INFORMATION: n is a, c, g, or t

<400> SEQUENCE: 36
aagtacaagt aaaatgaaag aaanatgtga agcctaggaa gaagaagtta acaagcctcc         60
ngtctctgat gcatgatgtt caagcacaag tgcagcagtc ttcaacattt agaagatggt        120
g                                                                        121

<210> SEQ ID NO 37
<211> LENGTH: 25
<212> TYPE: DNA
<213> ORGANISM: Zea mays

<400> SEQUENCE: 37
atgtgaagcc taggaagaag aagtt                                               25

<210> SEQ ID NO 38
<211> LENGTH: 23
<212> TYPE: DNA
<213> ORGANISM: Zea mays
```

```
<400> SEQUENCE: 38
tgcacttgtg cttgaacatc atg                                            23

<210> SEQ ID NO 39
<211> LENGTH: 16
<212> TYPE: DNA
<213> ORGANISM: Zea mays

<400> SEQUENCE: 39
caagcctcca gtctct                                                    16

<210> SEQ ID NO 40
<211> LENGTH: 15
<212> TYPE: DNA
<213> ORGANISM: Zea mays

<400> SEQUENCE: 40
aagcctcccg tctct                                                     15
```